(12) United States Patent
Yukawa et al.

(10) Patent No.: US 8,216,820 B2
(45) Date of Patent: *Jul. 10, 2012

(54) TRANSFORMANT OF CORYNEFORM BACTERIA CAPABLE OF PRODUCING ISOPROPANOL

(75) Inventors: Hideaki Yukawa, Kyoto (JP); Masayuki Inui, Kyoto (JP)

(73) Assignee: Research Institute of Innovative Technology for the Earth, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/988,882

(22) PCT Filed: Apr. 15, 2009

(86) PCT No.: PCT/JP2009/057547
§ 371 (c)(1),
(2), (4) Date: Nov. 17, 2010

(87) PCT Pub. No.: WO2009/131040
PCT Pub. Date: Oct. 29, 2009

(65) Prior Publication Data
US 2011/0165642 A1 Jul. 7, 2011

(30) Foreign Application Priority Data
Apr. 25, 2008 (JP) ................... 2008-116151

(51) Int. Cl.
*C12N 1/21* (2006.01)
*C12P 7/04* (2006.01)
(52) U.S. Cl. .............. 435/252.32; 435/252.3; 435/157
(58) Field of Classification Search .................. None
See application file for complete search history.

(56) References Cited

U.S. PATENT DOCUMENTS
4,965,197 A * 10/1990 Liebl et al. ............... 435/69.8
2008/0171371 A1 7/2008 Yukawa et al.

FOREIGN PATENT DOCUMENTS
WO 2005/026338 3/2005
WO 2006/028063 3/2006

OTHER PUBLICATIONS

International Search Report issued Jun. 9, 2009 in International (PCT) Application No. PCT/JP2009/057547.
International Preliminary Report on Patentability together with the English translation of the Written Opinion issued Dec. 13, 2010 in International (PCT) Application No. PCT/JP2009/057547.
Database entry entitled "Clostridium acetobutylicum NfrC homolog (nfrC) gene, partial cds; and thiolase A (thlA) gene, complete cds", Accession No. AF 072734, accessed Dec. 28, 2011, citing, e.g., FEMS Microbiol. Rev. 17 (3), 251-262 (1995).
Database entry entitled "Clostridium acetobutylicum alpha-amylase AmyA precursor (amyA) and acetoacetate decarboxylase (ads) genes, complete cds; and unknown genes", Accession No. M55392 M34078, accessed Aug. 24, 2011, citing, e.g., J. Bacteriol. 172 (12), 6907-6918 (1990).
Database entry entitled "*Escherichia coli* str. K-12 substr. MG1655, complete genome", Accession No. U00096 AE000111-AE000510, citing, e.g., Science 277 (5331), 1453-1474 (1997).
T. Hanai et al., "Engineered Synthetic Pathway for Isopropanol Production in *Escherichia coli*", Applied and Environmental Microbiology, vol. 73, No. 24, pp. 7814-7818, Dec. 2007.
T. Jojima et al., "Production of Isopropanol by Metabolically Engineered *Escherichia coli*", Applied Microbiol. Biotechnol., vol. 77, pp. 1219-1224, 2008.

* cited by examiner

*Primary Examiner* — Tekchand Saidha
*Assistant Examiner* — Md. Younus Meah
(74) *Attorney, Agent, or Firm* — Wenderoth, Lind & Ponack, L.L.P.

(57) ABSTRACT

A transformant capable of producing isopropanol which is constructed by transferring the following genes (a) to (d) into a coryneform bacterium:
(a) an exogenous gene which encodes an enzyme having acetyl-CoA acetyltransferase activity;
(b) an exogenous gene which encodes an enzyme having acetoacetyl CoA:acetate CoA-transferase activity;
(c) an exogenous gene which encodes an enzyme having acetoacetate decarboxylase activity; and
(d) an exogenous gene which encodes an enzyme having isopropanol dehydrogenase activity.

4 Claims, 3 Drawing Sheets

SEQUENCE LISTING

```
<160> NUMBER OF SEQ ID NOS: 24

<210> SEQ ID NO 1
<211> LENGTH: 44
<212> TYPE: DNA
<213> ORGANISM: Artificial sequence
<220> FEATURE:
<223> OTHER INFORMATION: Synthetic construct; Primer1

<400> SEQUENCE: 1
cgaattcaaa ggaggagtgt gttgatgaaa gaagttgtaa tagc                44

<210> SEQ ID NO 2
<211> LENGTH: 25
<212> TYPE: DNA
<213> ORGANISM: Artificial sequence
<220> FEATURE:
<223> OTHER INFORMATION: Synthetic construct; Primer2

<400> SEQUENCE: 2
ggatccctag cacttttcta gcaat                                    25

<210> SEQ ID NO 3
<211> LENGTH: 54
<212> TYPE: DNA
<213> ORGANISM: Artificial sequence
<220> FEATURE:
<223> OTHER INFORMATION: Synthetic construct; Primer3

<400> SEQUENCE: 3
ttcacacagg aaacaaagga ggagtgtgtt gatgttaaag gatgaagtaa ttaa    54

<210> SEQ ID NO 4
<211> LENGTH: 30
<212> TYPE: DNA
<213> ORGANISM: Artificial sequence
<220> FEATURE:
<223> OTHER INFORMATION: Synthetic construct; Primer4

<400> SEQUENCE: 4
cccgggttac ttaagataat catatataac                               30

<210> SEQ ID NO 5
<211> LENGTH: 48
<212> TYPE: DNA
```

<213> ORGANISM: Artificial sequence
<220> FEATURE:
<223> OTHER INFORMATION: Synthetic construct; Primer5

<400> SEQUENCE: 5
gaattcaaag gaggagtgtg ttgatgaaaa caaaattgat gacattac        48

<210> SEQ ID NO 6
<211> LENGTH: 26
<212> TYPE: DNA
<213> ORGANISM: Artificial sequence
<220> FEATURE:
<223> OTHER INFORMATION: Synthetic construct; Primer6

<400> SEQUENCE: 6
ggatcctcat aaatcacccc gttgcg        26

<210> SEQ ID NO 7
<211> LENGTH: 51
<212> TYPE: DNA
<213> ORGANISM: Artificial sequence
<220> FEATURE:
<223> OTHER INFORMATION: Synthetic construct; Primer7

<400> SEQUENCE: 7
ttcacacagg aaacaaagga ggagtgtgtt gatgaaagcc gtccagtaca c        51

<210> SEQ ID NO 8
<211> LENGTH: 22
<212> TYPE: DNA
<213> ORGANISM: Artificial sequence
<220> FEATURE:
<223> OTHER INFORMATION: Synthetic construct; Primer8

<400> SEQUENCE: 8
gatatcaggg aaccaccacg cc        22

<210> SEQ ID NO 9
<211> LENGTH: 22
<212> TYPE: DNA
<213> ORGANISM: Artificial sequence
<220> FEATURE:
<223> OTHER INFORMATION: Synthetic construct; Primer9

<400> SEQUENCE: 9
ggatccccat cggaagctgt gg        22

<210> SEQ ID NO 10
<211> LENGTH: 19
<212> TYPE: DNA
<213> ORGANISM: Artificial sequence
<220> FEATURE:
<223> OTHER INFORMATION: Synthetic construct; Primer10

<400> SEQUENCE: 10
tgtttcctgt gtgaaattg        19

<210> SEQ ID NO 11
<211> LENGTH: 21
<212> TYPE: DNA
<213> ORGANISM: Artificial sequence
<220> FEATURE:
<223> OTHER INFORMATION: Synthetic construct; Primer11

<400> SEQUENCE: 11
gcatgccatc ggaagctgtg g        21

```
<210> SEQ ID NO 12
<211> LENGTH: 22
<212> TYPE: DNA
<213> ORGANISM: Artificial sequence
<220> FEATURE:
<223> OTHER INFORMATION: Synthetic construct; Primer12

<400> SEQUENCE: 12
cccgggccat cggaagctgt gg                                              22

<210> SEQ ID NO 13
<211> LENGTH: 1179
<212> TYPE: DNA
<213> ORGANISM: Clostridium acetobutylicum
<220> FEATURE:
<221> NAME/KEY: misc_feature
<222> LOCATION: (1)..(1179)
<223> OTHER INFORMATION: thl

<400> SEQUENCE: 13
atgaaagaag ttgtaatagc tagtgcagta agaacagcga ttggatctta tggaaagtct      60
cttaaggatg taccagcagt agatttagga gctacagcta taaaggaagc agttaaaaaa     120
gcaggaataa aaccagagga tgttaatgaa gtcattttag gaaatgttct tcaagcaggt     180
ttaggacaga atccagcaag acaggcatct tttaaagcag gattaccagt tgaaattcca     240
gctatgacta ttaataaggt ttgtggttca ggacttagaa cagttagctt agcagcacaa     300
attataaaag caggagatgc tgacgtaata atagcaggtg gtatggaaaa atgtctaga      360 gctccttact tagcgaataa cgctagatgg ggatatagaa tgggaaacgc taaatttgtt     420
gatgaaatga tcactgacgg attgtgggat gcatttaatg attaccacat gggaataaca     480
gcagaaaaca tagctgagag atggaacatt tcaagagaag aacaagatga gtttgctctt     540
gcatcacaaa aaaaagctga agaagctata aaatcaggtc aatttaaaga tgaaatagtt     600
cctgtagtaa ttaaaggcag aaagggagaa actgtagttg atacagatga gcaccctaga     660
tttggatcaa ctatagaagg acttgcaaaa ttaaaacctg ccttcaaaaa agatggaaca     720
gttacagctg gtaatgcatc aggattaaat gactgtgcag cagtacttgt aatcatgagt     780
gcagaaaaag ctaaagagct tggagtaaaa ccacttgcta agatagtttc ttatggttca     840
gcaggagttg acccagcaat aatgggatat ggaccttttct atgcaacaaa agcagctatt     900
gaaaaagcag gttggacagt tgatgaatta gatttaatag aatcaaatga agcttttgca     960
gctcaaagtt tagcagtagc aaaagattta aaatttgata tgaataaagt aaatgtaaat    1020
ggaggagcta ttgccccttg gtcatccaatt ggagcatcag gtgcaagaat actcgttact    1080
cttgtacacg caatgcaaaa aagagatgca aaaaaggct tagcaacttt atgtataggt    1140
ggcggacaag gaacagcaat attgctagaa aagtgctag                            1179

<210> SEQ ID NO 14
<211> LENGTH: 1313
<212> TYPE: DNA
<213> ORGANISM: Escherichia coli
<220> FEATURE:
<221> NAME/KEY: misc_feature
<222> LOCATION: (1)..(1313)
<223> OTHER INFORMATION: atoAD

<400> SEQUENCE: 14
atgaaaacaa aattgatgac attacaagac gccaccggct tctttcgtga cggcatgacc      60
atcatggtgg gcggatttat ggggattggc actccatccc gcctggttga agcattactg     120
```

```
gaatctggtg ttcgcgacct gacattgata gccaatgata ccgcgtttgt tgataccggc    180
atcggtccgc tcatcgtcaa tggtcgagtc cgcaaagtga ttgcttcaca tatcggcacc    240
aacccggaaa caggtcggcg catgatatct ggtgagatgg acgtcgttct ggtgccgcaa    300
ggtacgctaa tcgagcaaat cgctgtggt ggagctggac ttggtggttt tctcacccca    360
acgggtgtcg gcaccgtcgt agaggaaggc aaacagacac tgacactcga cggtaaaacc    420
tggctgctcg aacgcccact cgcgccgac ctggcgctaa ttcgcgctca tcgttgcgac    480
acacttggca acctgaccta tcaacttagc gcccgcaact ttaaccccct gatagccctt    540
gcggctgata tcacgctggt agagccagat gaactggtcg aaaccggcga gctgcaacct    600
gaccatattg tcacccctgg tgccgttatc gaccacatca tcgtttcaca ggagagcaaa    660
taatggatgc gaaacaacgt attgcgcgcc gtgtggcgca agagcttcgt gatggtgaca    720
tcgttaactt agggatcggt ttacccacaa tggtcgccaa ttatttaccg gagggtattc    780
atatcactct gcaatcggaa aacggcttcc tcggtttagg cccggtcacg acagcgcatc    840
cagatctggt gaacgctggc gggcaaccgt gcggtgtttt acccggtgca gccatgtttg    900
atagcgccat gtcatttgcg ctaatccgtg gcggtcatat tgatgcctgc gtgctcggcg    960
gtttgcaagt agacgaagaa gcaaacctcg cgaactgggt agtgcctggg aaaatggtgc   1020
ccggtatggg tggcgcgatg gatctggtga ccgggtcgcg caaagtgatc atcgccatgg   1080
aacattgcgc caaagatggt tcagcaaaaa ttttgcgccg ctgcaccatg ccactcactg   1140
cgcaacatgc ggtgcatatg ctggttactg aactggctgt ctttcgtttt attgacggca   1200
aaatgtggct caccgaaatt gccgacgggt gtgatttagc caccgtgcgt gccaaaacag   1260
aagctcggtt tgaagtcgcc gccgatctga atacgcaacg gggtgattta tga          1313
```

<210> SEQ ID NO 15  
<211> LENGTH: 968  
<212> TYPE: DNA  
<213> ORGANISM: Clostridium acetobutylicum  
<220> FEATURE:  
<221> NAME/KEY: misc_feature  
<222> LOCATION: (1)..(968)  
<223> OTHER INFORMATION: adc

<400> SEQUENCE: 15

```
gcatgccatc ggaagctgtg gtatggctgt gcaggtcgta aatcactgca taattcgtgt     60
cgctcaaggc gcactcccgt tctggataat gttttttgcg ccgacatcat aacggttctg    120
gcaaatattc tgaaatgagc tgttgacaat taatcatcgg ctcgtataat gtgtggaatt    180
gtgagcggat aacaatttca cacaggaaac aaggaggag tgtgttgatg ttaaaggatg    240
aagtaattaa acaaattagc acgccattaa cttcgcctgc atttcctaga ggaccctata    300
aatttcataa tcgtgagtat tttaacattg tatatcgtac agatatggat gcacttcgta    360
aagttgtgcc agagcccttta gaaattgatg agcccttagt caggtttgaa attatggcaa    420
tgcatgatac gagtggactt ggttgttata cagaaagcgg acaggctatt cccgtaagct    480
ttaatggagt taagggagat tatcttcata tgatgtattt agataatgag cctgcaattg    540
cagtaggaag ggaattaagt gcatatccta aaaagctcgg gtatccaaag cttttttgtgg    600 attcagatac tttagtagga actttagact atggaaaact tagagttgcg acagctacaa    660
tggggtacaa acataaagcc ttagatgcta atgaagcaaa ggatcaaatt tgtcgcccta    720
attatatgtt gaaaataata cccaattatg atggaagccc tagaatatgt gagcttataa    780
atgcgaaaat cacagatgtt accgtacatg aagcttggac aggaccaact cgactgcagt    840
```

| | |
|---|---:|
| tatttgatca cgctatggcg ccacttaatg atttgccagt aaaagagatt gtttctagct | 900 |
| ctcacattct tgcagatata atattgccta gagctgaagt tatatatgat tatcttaagt | 960 |
| aacccggg | 968 |

<210> SEQ ID NO 16
<211> LENGTH: 1038
<212> TYPE: DNA
<213> ORGANISM: Rhodococcus ruber
<220> FEATURE:
<221> NAME/KEY: misc_feature
<222> LOCATION: (1)..(1038)
<223> OTHER INFORMATION: adh

<400> SEQUENCE: 16

| | |
|---|---:|
| atgaaagccg tccagtacac cgagatcggc tccgagccgg tcgttgtcga catccccacc | 60 |
| ccgacgcccg ggccgggtga gatcctgctg aaggtcaccg cggccgggct gtgccactcg | 120 |
| gacatcttcg tgatggacat gccggcggcg cagtacgcct acggcctgcc gctcacccta | 180 |
| ggccacgagg gtgtcggcac cgtcgccgaa ctcggcgagg gcgtcacggg attcggggtg | 240 |
| ggggacgccg tcgccgtgta cgggccgtgg ggctgcggtg cgtgccacgc ctgcgcgcgc | 300 |
| ggccgggaga actactgcac ccgcgccgcc gacctgggca tcacgccacc cggtctcggc | 360 |
| tcgcccggat cgatggccga gtacatgatc gtcgattcgg cgcgccacct cgtcccgatc | 420 |
| ggagacctcg acccggtcgc cgcggcgccg ctcaccgacg ccggtctgac gccgtaccac | 480 |
| gcgatctccc gggtcctgcc gctgctgggg ccgggctcga cggccgtcgt catcggtgtc | 540 |
| ggcgggctcg gccacgtcgg catccagatc ctgcgcgccg tcagcgcggc ccgtgtgatc | 600 |
| gccgtcgacc tcgacgacga ccgtctcgcc ctcgcccgcg aggtcggcgc cgacgcggcg | 660 |
| gtgaagtcgg gcgccggtgc ggcggacgcg atccgggaac tgaccggcgg ccagggcgcg | 720 |
| acggcggtgt tcgacttcgt cggcgcccag tcgacgatcg acacggcgca gcaggtggtc | 780 |
| gcggtcgacg ggcacatctc ggtcgtgggc atccacgccg gcgcacacgc caaggtcggg | 840 |
| ttcttcatga tcccgttcgg cgcctccgtc gtgaccccgt actggggcac ccggtcggaa | 900 |
| ctgatggagg tcgtcgcgct ggcccgcgcc ggccggctgg acatccacac cgagacgttc | 960 |
| accctcgacg aggggccggc ggcgtaccgg cggctgcgcg agggcagcat ccgcggccgc | 1020 |
| ggcgtggtgg ttccctga | 1038 |

<210> SEQ ID NO 17
<211> LENGTH: 8722
<212> TYPE: DNA
<213> ORGANISM: Artificial sequence
<220> FEATURE:
<223> OTHER INFORMATION: Synthetic construct; Plasmid pCRC203

<400> SEQUENCE: 17

| | |
|---|---:|
| atgaccatga ttacgaatta attcgagctc aggcagccat cggaagctgt ggtatggctg | 60 |
| tgcaggtcgt aaatcactgc ataattcgtg tcgctcaagg cgcactcccg ttctggataa | 120 |
| tgttttttgc gccgacatca taacggttct ggcaaatatt ctgaaatgag ctgttgacaa | 180 |
| ttaatcatcg gctcgtataa tgtgtggaat tgtgagcgga taacaatttc acacaggaaa | 240 |
| cagaattccc gggaattcaa aggaggagtg tgttgatgaa agaagttgta atagctagtg | 300 |
| cagtaagaac agcgattgga tcttatggaa agtctcttaa ggatgtacca gcagtagatt | 360 |
| taggagctac agctataaag gaagcagtta aaaagcagg aataaaacca gaggatgtta | 420 |
| atgaagtcat tttaggaaat gttcttcaag caggtttagg acagaatcca gcaagacagg | 480 |

-continued

```
catcttttaa agcaggatta ccagttgaaa ttccagctat gactattaat aaggtttgtg      540
gttcaggact tagaacagtt agcttagcag cacaaaattat aaaagcagga gatgctgacg      600
taataatagc aggtggtatg gaaaatatgt ctagagctcc ttacttagcg aataacgcta      660 gatgggata tagaatggga aacgctaaat ttgttgatga aatgatcact gacggattgt       720
gggatgcatt taatgattac cacatgggaa taacagcaga aaacatagct gagagatgga      780
acatttcaag agaagaacaa gatgagtttg ctcttgcatc acaaaaaaaa gctgaagaag      840
ctataaaatc aggtcaattt aaagatgaaa tagttcctgt agtaattaaa ggcagaaagg      900
gagaaactgt agttgataca gatgagcacc ctagatttgg atcaactata aaggacttg      960 caaaattaaa acctgccttc aaaaaagatg aaacagttac agctggtaat gcatcaggat     1020
taaatgactg tgcagcagta cttgtaatca tgagtgcaga aaaagctaaa gagcttggag     1080
taaaaccact tgctaagata gtttcttatg gttcagcagg agttgaccca gcaataatgg     1140
gatatggacc tttctatgca acaaaagcag ctattgaaaa agcaggttgg acagttgatg     1200
aattagattt aatagaatca aatgaagctt ttgcagctca aagtttagca gtagcaaaag     1260
atttaaaatt tgatatgaat aaagtaaatg taaatggagg agctattgcc cttggtcatc     1320
caattggagc atcaggtgca agaatactcg ttactcttgt acacgcaatg caaaaaagag     1380
atgcaaaaaa aggcttagca actttatgta taggtggcgg acaaggaaca gcaatattgc     1440
tagaaaagtg ctagggatcc ccatcggaag ctgtggtatg gctgtgcagg tcgtaaatca     1500
ctgcataatt cgtgtcgctc aaggcgcact cccgttctgg ataatgtttt ttgcgccgac     1560
atcataacgg ttctggcaaa tattctgaaa tgagctgttg acaattaatc atcggctcgt     1620
ataatgtgtg gaattgtgag cggataacaa tttcacacag aaacaaagg aggagtgtgt      1680 tgatgaaaac aaaattgatg acattacaag acgccaccgg cttctttcgt gacggcatga     1740
ccatcatggt gggcggattt atggggattg gcactccatc ccgcctggtt gaagcattac     1800
tggaatctgg tgttcgcgac ctgacattga tagccaatga taccgcgttt gttgataccg     1860
gcatcggtcc gctcatcgtc aatggtcgag tccgcaaagt gattgcttca catatcggca     1920
ccaacccgga aacaggtcgg cgcatgatat ctggtgagat ggacgtcgtt ctggtgccgc     1980
aaggtacgct aatcgagcaa attcgctgtg gtggagctgg acttggtggt tttctcaccc     2040
caacgggtgt cggcaccgtc gtagaggaag gcaaacagac actgacactc gacggtaaaa     2100
cctggctgct cgaacgccca ctgcgcgccg acctggcgct aattcgcgct catcgttgcg     2160
acacacttgg caacctgacc tatcaactta gcgcccgcaa cttttaacccc ctgatagccc     2220 ttgcggctga tatcacgctg gtagagccag atgaactggt cgaaaccggc gagctgcaac     2280
ctgaccatat tgtcacccct ggtgccgtta tcgaccacat catcgtttca caggagagca     2340
aataatggat gcgaaacaac gtattgcgcg ccgtgtggcg caagagcttc gtgatggtga     2400
catcgttaac ttagggatcg gtttacccac aatggtcgcc aattatttac cggagggtat     2460
tcatatcact ctgcaatcgg aaaacggctt cctcggttta ggcccggtca cgacagcgca     2520
tccagatctg gtgaacgctg gcgggcaacc gtgcggtgtt ttacccggtg cagccatgtt     2580
tgatagcgcc atgtcatttg cgctaatccg tggcggtcat attgatgcct gcgtgctcgg     2640
cggtttgcaa gtagacgaag aagcaaacct cgcgaactgg gtagtgcctg ggaaaatggt     2700
gcccggtatg ggtggcgcga tggatctggt gaccgggtcg cgcaaagtga tcatcgccat     2760
ggaacattgc gccaaagatg gttcagcaaa atttttgcgc cgctgcacca tgccactcac     2820
tgcgcaacat gcggtgcata tgctggttac tgaactggct gtctttcgtt ttattgacgg     2880
```

```
caaaatgtgg ctcaccgaaa ttgccgacgg gtgtgattta gccaccgtgc gtgccaaaac    2940
agaagctcgg tttgaagtcg ccgccgatct gaatacgcaa cggggtgatt tatgacatgc    3000
catcggaagc tgtggtatgg ctgtgcaggt cgtaaatcac tgcataattc gtgtcgctca    3060
aggcgcactc ccgttctgga taatgttttt tgcgccgaca tcataacggt tctggcaaat    3120
attctgaaat gagctgttga caattaatca tcggctcgta taatgtgtgg aattgtgagc    3180
ggataacaat ttcacacagg aaacaaagga ggagtgtgtt gatgttaaag gatgaagtaa    3240
ttaaacaaat tagcacgcca ttaacttcgc ctgcatttcc tagaggaccc tataaatttc    3300
ataatcgtga gtattttaac attgtatatc gtacagatat ggatgcactt cgtaaagttg    3360
tgccagagcc tttagaaatt gatgagccct tagtcaggtt tgaaattatg gcaatgcatg    3420
atacgagtgg acttggttgt tatacagaaa gcggacaggc tattcccgta agctttaatg    3480
gagttaaggg agattatctt catatgatgt atttagataa tgagcctgca attgcagtag    3540
gaagggaatt aagtgcatat cctaaaaagc tcgggtatcc aaagcttttt gtggattcag    3600
atactttagt aggaacttta gactatggaa aacttagagt tgcgacagct acaatggggt    3660
acaaacataa agccttagat gctaatgaag caaaggatca aatttgtcgc cctaattata    3720
tgttgaaaat aatacccaat tatgatggaa gccctagaat atgtgagctt ataaatgcga    3780
aaatcacaga tgttaccgta catgaagctt ggacaggacc aactcgactg cagttatttg    3840
atcacgctat ggcgccactt aatgatttgc cagtaaaaga gattgtttct agctctcaca    3900
ttcttgcaga tataatattg cctagagctg aagttatata tgattatctt aagtaacccg    3960
gggtcgacct gcagccaagc ttggctgttt tggcggatga gagaagattt tcagcctgat    4020
acagattaaa tcagaacgca gaagcggtct gataaaacag aatttgcctg gcggcagtag    4080
cgcggtggtc ccacctgacc ccatgccgaa ctcagaagtg aaacgccgta cgccgatgg    4140
tagtgtgggg tctccccatg cgagagtagg gaactgccag gcatcaaata aaacgaaagg    4200
ctcagtcgaa agactgggcc tttcgtttta tctgttgttt gtcggtgaac gctctcctga    4260
gtaggacaaa tccgccggga gcggatttga acgttgcgaa gcaacggccc ggagggtggc    4320
gggcaggacg cccgccataa actgccaggc atcaaattaa gcagaaggcc atcctgacgg    4380
atggcctttt tgcgtttcta caaactcttt tgtttatttt tctaaataca ttcaaatatg    4440
tatccgctca tgagacaata accctgataa atgcttcaat aatattgaaa aaggaagagt    4500
atgagtattc aacatttccg tgtcgccctt attcccttt ttgcggcatt ttgccttcct    4560
gttttgctc acccagaaac gctggtgaaa gtaaaagatg ctgaagatca gttgggtgca    4620
cgagtgggtt acatcgaact ggatctcaac agcggtaaga tccttgagag ttttcgcccc    4680
gaagaacgtt ttccaatgat gagcactttt aaagttctgc tatgtggcat gcaagctagc    4740
ttggcactgg ccgtcgtttt acaacgtcgt gactgggaaa accctggcgt tacccaactt    4800
aatcgccttg cagcacatcc cccttcgcc agctggcgta atagcgaaga ggcccgcacc    4860
gatcgccctt cccaacagtt gcgcagcctg aatggcgaat gagcttcttc cgcttcctcg    4920
ctcactgact cgctgcgctc ggtcgttcgg ctgcggcgag cggtatcagc tcactcaaag    4980
gcggtaatac ggttatccac agaatcaggg gataacgcag gaaagaacat gtgagcaaaa    5040
ggccagcaaa aggccaggaa ccgtaaaaag gccgcgttgc tggcgttttt ccataggctc    5100
cgcccccctg acgagcatca caaaaatcga cgctcaagtc agaggtggcg aaacccgaca    5160
ggactataaa gataccaggc gtttccccct ggaagctccc tcgtgcgctc tcctgttccg    5220
accctgccgc ttaccggata cctgtccgcc tttctccctt cgggaagcgt ggcgctttct    5280
```

```
caatgctcac gctgtaggta tctcagttcg gtgtaggtcg ttcgctccaa gctgggctgt    5340
gtgcacgaac ccccgttca gcccgaccgc tgcgccttat ccggtaacta tcgtcttgag    5400
tccaacccgg taagacacga cttatcgcca ctggcagcag ccactggtaa caggattagc    5460
agagcgaggt atgtaggcgg tgctacagag ttcttgaagt ggtggcctaa ctacggctac    5520
actagaagga cagtatttgg tatctgcgct ctgctgaagc cagttacctt cggaaaaaga    5580
gttggtagct cttgatccgg caaacaaacc accgctggta gcggtggttt ttttgtttgc    5640
aagcagcaga ttacgcgcag aaaaaaagga tctcaagaag atcctttgat cttttctacg    5700
gggtctgacg ctcagtggaa cgataacaca tgcagtcatg tcgtgctaat gtgtaaaaca    5760
tgtacatgca gattgctggg ggtgcagggg gcggagccac cctgtccatg cggggtgtgg    5820
ggcttgcccc gccggtacag acagtgagca ccggggcacc tagtcgcgga tacccccct    5880
aggtatcgga cacgtaaccc tcccatgtcg atgcaaatct ttaacattga gtacgggtaa    5940
gctggcacgc atagccaagc taggcggcca ccaaacacca ctaaaaatta atagtcccta    6000
gacaagacaa accccgtgc gagctaccaa ctcatatgca cgggggccac ataacccgaa    6060
ggggtttcaa ttgacaacca tagcactagc taagacaacg ggcacaacac ccgcacaaac    6120
tcgcactgcg caaccccgca caacatcggg tctaggtaac actgaaatag aagtgaacac    6180
ctctaaggaa ccgcaggtca atgagggttc taaggtcact cgcgctaggg cgtggcgtag    6240
gcaaaacgtc atgtacaaga tcaccaatag taaggctctg gcggggtgcc ataggtggcg    6300
cagggacgaa gctgttgcgg tgtcctggtc gtctaacggt gcttcgcagt ttgagggtct    6360
gcaaaactct cactctcgct gggggtcacc tctggctgaa ttggaagtca tgggcgaacg    6420
ccgcattgag ctggctattg ctactaagaa tcacttggcg gcgggtggcg cgctcatgat    6480
gtttgtgggc actgttcgac acaaccgctc acagtcattt gcgcaggttg aagcgggtat    6540
taagactgcg tactcttcga tggtgaaaac atctcagtgg aagaaagaac gtgcacggta    6600
cggggtggag cacacctata gtgactatga ggtcacagac tcttgggcga acggttggca    6660
cttgcaccgc aacatgctgt tgttcttgga tcgtccactg tctgacgatg aactcaaggc    6720
gtttgaggat tccatgtttt cccgctggtc tgctggtgtg gttaaggccg gtatggacgc    6780
gccactgcgt gagcacgggg tcaaacttga tcaggtgtct acctggggtg gagacgctgc    6840
gaaaatggca acctacctcg ctaagggcat gtctcaggaa ctgactggct ccgctactaa    6900
aaccgcgtct aaggggtcgt acacgccgtt tcagatgttg gatatgttgg ccgatcaaag    6960
cgacgccggc gaggatatgg acgctgtttt ggtggctcgg tggcgtgagt atgaggttgg    7020
ttctaaaaac ctgcgttcgt cctggtcacg tggggctaag cgtgctttgg gcattgatta    7080
catagacgct gatgtacgtc gtgaaatgga agaagaactg tacaagctcg ccggtctgga    7140
agcaccggaa cgggtcgaat caacccgcgt tgctgttgct ttggtgaagc ccgatgattg    7200
gaaactgatt cagtctgatt tcgcggttag gcagtacgtt ctagattgcg tggataaggc    7260
taaggacgtg gccgctgcgc aacgtgtcgc taatgaggtg ctggcaagtc tgggtgtgga    7320
ttccaccccg tgcatgatcg ttatggatga tgtggacttg gacgcggttc tgcctactca    7380
tggggacgct actaagcgtg atctgaatgc ggcggtgttc gcgggtaatg agcagactat    7440
tcttcgcacc cactaaaagc ggcataaacc ccgttcgata tttttgtgcga tgaatttatg    7500
gtcaatgtcg cggggcaaa ctatgatggg tcttgttgtg ttatctccgt cgaacggaag    7560
atcacttcgc agaataaata aatcctggta tccctgttga taccgggaag ccctgggcca    7620
acttttggcg aaaatgagac gttgatcggc acgtaagagg ttccaacttt caccataatg    7680
```

-continued

```
aaataagatc actaccgggc gtattttttg agttatcgag attttcagga gctaaggaag    7740
ctaaaatgga gaaaaaaatc actggatata ccaccgttga tatatcccaa tggcatcgta    7800
aagaacattt tgaggcattt cagtcagttg ctcaatgtac ctataaccag accgttcagc    7860
tggatattac ggcctttttta aagaccgtaa agaaaaataa gcacaagttt tatccggcct    7920
ttattcacat tcttgcccgc ctgatgaatg ctcatccgga atttcgtatg gcaatgaaag    7980
acggtgagct ggtgatatgg gatagtgttc acccttgtta ccgttttc catgagcaaa     8040 ctgaaacgtt ttcatcgctc tggagtgaat accacgacga tttccggcag tttctacaca    8100
tatattcgca agatgtggcg tgttacggtg aaaacctggc ctatttccct aaagggttta    8160
ttgagaatat gttttcgtc tcagccaatc cctgggtgag tttcaccagt tttgatttaa     8220
acgtggccaa tatggacaac ttcttcgccc ccgttttcac catgggcaaa tattatacgc    8280
aaggcgacaa ggtgctgatg ccgctggcga ttcaggttca tcatgccgtc tgtgatggct    8340
tccatgtcgg cagaatgctt aatgaattac aacagtactg cgatgagtgg cagggcgggg    8400
cgtaattttt ttaaggcagt tattggtgcc cttaaacgcc tggtgctacg cctgaataag    8460
tgataataag cggatgaatg gcagaaattc agcttggccc agtgccaagc tccaatacgc    8520
aaaccgcctc tccccgcgcg ttggccgatt cattaatgca gctggcacga caggtttccc    8580
gactggaaag cgggcagtga gcgcaacgca attaatgtga gttagctcac tcattaggca    8640
ccccaggctt tacactttat gcttccggct cgtatgttgt gtggaattgt gagcggataa    8700
caatttcaca caggaaacag ct                                              8722

<210> SEQ ID NO 18
<211> LENGTH: 30
<212> TYPE: DNA
<213> ORGANISM: Artificial sequence
<220> FEATURE:
<223> OTHER INFORMATION: Synthetic construct; Primer13

<400> SEQUENCE: 18
ctcttctaga cctcaataga gtcttcagat                                       30

<210> SEQ ID NO 19
<211> LENGTH: 30
<212> TYPE: DNA
<213> ORGANISM: Artificial sequence
<220> FEATURE:
<223> OTHER INFORMATION: Synthetic construct; Primer14

<400> SEQUENCE: 19
ctcttctaga tgctcagtat gaatggcctt                                       30

<210> SEQ ID NO 20
<211> LENGTH: 6625
<212> TYPE: DNA
<213> ORGANISM: Artificial sequence
<220> FEATURE:
<223> OTHER INFORMATION: Synthetic construct; Plasmid pCRA725-SSI11

<400> SEQUENCE: 20
tcgacggatc gttccactga gcgtcagacc ccgtagaaaa gatcaaagga tcttcttgag      60
atcctttttt tctgcgcgta atctgctgct tgcaaacaaa aaaaccaccg ctaccagcgg     120
tggtttgttt gccggatcaa gagctaccaa ctctttttcc gaaggtaact ggcttcagca    180
gagcgcagat accaaatact gtccttctag tgtagccgta gttaggccac cacttcaaga    240
actctgtagc accgcctaca tacctcgctc tgctaatcct gttaccagtg gctgctgcca    300
```

-continued

```
gtggcgataa gtcgtgtctt accgggttgg actcaagacg atagttaccg gataaggcgc    360
agcggtcggg ctgaacgggg ggttcgtgca cacagcccag cttggagcga acgacctaca    420
ccgaactgag atacctacag cgtgagcatt gagaaagcgc cacgcttccc gaagggagaa    480
aggcggacag gtatccggta agcggcaggg tcggaacagg agagcgcacg agggagcttc    540 caggggaaa cgcctggtat ctttatagtc ctgtcgggtt tcgccacctc tgacttgagc     600 gtcgatttt gtgatgctcg tcaggggggc ggagcctatg gaaaaacgcc agcaacgcgg     660
cctttttacg gttcctggcc ttttgctggc cttttgctca catgttcttt cctgcgttat    720
cccctgattc tgtggataac cgtattaccg cctttgagtg agctgatacc gctcgccgca    780
gccgaacgac cgagcgcagc gagtcagtga gcgaggaagc ggaagaagct cgcacattca    840
gcagcgtttt tcagcgcgtt ttcgatcagc gtttcaatgt tggtatcaac accaggttta    900
actttgaact tatcggcact gacggttact gattttgaac ttttgctttg ccacggaacg    960
gtctgcgttg tcgggaagat gcgtgatctg atccttcaac tcagcaaaag ttcgccaata   1020
cgcaaaccgc ctctccccgc gcgttggccg attcattaat gcagctggca cgacaggttt   1080
cccgactgga aagcgggcag tgagcgcaac gcaattaatg tgagttagct cactcattag   1140 gcacccagg ctttacactt tatgcttccg gctcgtatgt tgtgtggaat tgtgagcgga    1200
taacaatttc acacaggaaa cagctatgac catgattacg aattcgagct cggtacccgg   1260
ggatcctcta gacctcaata gagtcttcag atacaagcgc ttcactctac agcgcagtag   1320
ggttcgcgct attcggattc acttaccttg gagttgcttt gggaacctca ttatctgcag   1380
acaatcgtgg cttgggcgtt tattgtggat gggctcctgt tattgcaggc cttcttgtat   1440
atgtgaatgc cactacactc tcagatccta cactttcagt gttgtgggca tcatgggtat   1500
tactcttcgt ggctttctgt atcgccctca ctcgaaccgc aacattttgg tcatatgcag   1560
ccggagtctt agctgtgtac caagcattca gcaccgcaac cattcccgcg ttactattaa   1620
ttcatgagtc tccacttgca ttgattcaaa ttgcgggagc attgatctgc gtcatcgcac   1680
tattcaggcg gcagaatcag tccaagtcgc ttgaacctca acgctcatga ctcttaccga   1740
aattatccaa cgacttgtcc ccgtattggt ttttgtcgct tcaatgtctg ttgttgtaaa   1800
tctctcggcc gcagtgggtg caataacaag aatcactgaa atccttcaaa gtatcagcaa   1860
aggatctgca tggggaactt ggtggctagt catgctcata tcgaccgttt caacagtctt   1920
cttgtccttg gatacaactg ctattcttgt gactcctttg gccatagcgc tcgcggaaag   1980
agtcgggcta gctgtatttc ccttggtact cggcgtgatc tggattgcga atttaggttc   2040
cttaaccatc ccggtatcca atctgacgaa cttactctct gtatctggcg ggatgtttgt   2100
aggaacttca gactatttca gcctgtcatg gaagccagca ctcgcgacaa caatcgtagc   2160
attcgccgga ggagcaattg ctttcatttt gagaaacccc tcttcgatac acagacaatc   2220
acgtcccccg tcttctttag atacagcgca agagaattcg acatctcagg ttcattgcct   2280
agtcacatta ggtgtacttg ttccggtctt ggcatcgccg attccctatt ggatatcaag   2340
cacggtagct gcaatctatc tgctgctgat ttttagcgcc agcaaaagaa gccgaatcat   2400
tctttcatgg acgttaatcc cgtggagctc cctattcttt gtctctggac tatcacttat   2460 ggcattttc ctgcatacac aaagtgatgt cattgcagaa gaattctcat ctcttttgaa    2520
ttccaccggg atggggcctg tattgcttac cgccagcggt gcgatcttag ccaatttgat   2580
caacaacatt ccagcttttc tagcactcga accagccgca accagcccac agagcatgat   2640
gttcctaata attggagtaa atgcaggccc gattgtagcc ccgtgggctt cgctggcgac   2700
```

```
tctattgtgt ttggatcagg ccaagcgcaa cggattcaat atcccttggc ggccaatcat    2760
cctctgcgga atgacacttt ttccttttgc tattctccta cctctcgccg ctactttaat    2820
ttgatagctc acaaggtctc tattacatgg aaatcaaaac catcagctcg agctaaatta    2880
acagtctgca ctgcttggtt accttcaaac cgaataattc cgcgtggccc ttcgaaagtc    2940
agaccatcga tgatgctgtt gaatccttcg actgttaagc cacgagaacg ttgagccaga    3000
tgtgcaaggg tataaatacc ttgataacaa gactgcgcca tattgttcag cgcaggggca    3060
gttacgccgg cggtctttga atacctacct acaaaatcaa gagcttcggg gctggttaag    3120
ctccggaagt atgaagctga ggaaaagaga ttgtcgtgg cttcgtagcc acttgctaac    3180
aacatattct cttccatcag cgggctgtac ctggtgattt tctcggaaag cccggcttca    3240
gcaaagtttc tgttgaaatc gactgcgtcc tgcccaacca aaagcatcaa cacaccatcg    3300
caaccactgg cggcaacttc gccaggaagc tgtggagctg cgccttctcc cattttatg    3360 aaagagctac ccacaatatc tatgccaagc agtgaagaca tagacacaat cttctcaaat    3420
gacctcaaag gccattcata ctgagcatct agagtcgacc tgcaggcatg caagcttggc    3480
actggccgtc gttttacaac gtcgtgactg gaaaaccct ggcgttaccc aacttaatcg    3540
ccttgcagca catcccccctt tcgccagctg gcgtaatagc gaagaggccc gcaccgatcg    3600
cccttcccaa cagttgcgca gcctgaatgg cgaatgcgat ttattcaaca aagccgccgt    3660
cccgtcaagt cagcgtaatg ctctgccagt gttacaacca attaaccaat tctgattaga    3720
aaaactcatc gagcatcaaa tgaaactgca atttattcat atcaggatta tcaataccat    3780
atttttgaaa aagccgtttc tgtaatgaag gagaaaactc accgaggcag ttccatagga    3840
tggcaagatc ctggtatcgg tctgcgattc cgactcgtcc aacatcaata caacctatta    3900
atttcccctc gtcaaaaata aggttatcaa gtgagaaatc accatgagtg acgactgaat    3960
ccggtgagaa tggcaaaagc ttatgcattt cttttccagac ttgttcaaca ggccagccat    4020
tacgctcgtc atcaaaatca ctcgcatcaa ccaaaccgtt attcattcgt gattgcgcct    4080
gagcgagacg aaatacgcga tcgctgttaa aaggacaatt acaaacagga tcgaatgca    4140 accggcgcag gaacactgcc agcgcatcaa caatattttc acctgaatca ggatattctt    4200
ctaatacctg gaatgctgtt ttcccgggga tcgcagtggt gagtaaccat gcatcatcag    4260
gagtacggat aaaatgcttg atggtcggaa gaggcataaa ttccgtcagc cagtttagtc    4320
tgaccatctc atctgtaaca tcattggcaa cgctaccttt gccatgtttc agaaacaact    4380
ctggcgcatc gggcttccca tacaatcgat agattgtcgc acctgattgc ccgacattat    4440
cgcgagccca tttataccca tataaatcag catccatgtt ggaatttaat cgcggcttcg    4500
agcaagacgt ttcccgttga atatggctca taacacccct tgtattactg tttatgtaag    4560
cagacagttt tattgttcat gatgatatat ttttatcttg tgcaatgtaa catcagagat    4620
tttgagacac aacgtggctt tgttgaataa atcgaacttt tgctgagttg aaggatcaga    4680
tcacgcatct tcccgacaac gcagaccgtt ccgtggcaaa gcaaaagttc aaaatcacca    4740
actggtccac ctacaacaaa gctctcatca accgtggctc cctcactttc tggctggatg    4800 atgggcgat tcaggatcca taattcgtgt cgctcaaggc gcactcccgt tctggataat    4860
gttttttgcg ccgacatcat aacggttctg gcaaatattc tgaaatgagc tgttgacaat    4920
taatcatcgg ctcgtataat gtgtggaatt gtgagcggat aacaatttca cacaggaaac    4980
agaattgata aagcaggcaa gacctaaaat gtgtaaaggg caaagtgtat actttggcgt    5040
caccccttac atatttttagg tcttttttta ttgtgcgtaa ctaacttgcc atcttcaaac    5100
```

```
aggagggctg gaagaagcag accgctaaca cagtacataa aaaggagac atgaacgatg    5160 aacatcaaaa agtttgcaaa acaagcaaca gtattaacct ttactaccgc actgctggca    5220
ggaggcgcaa ctcaagcgtt tgcgaaagaa acgaaccaaa agccatataa ggaaacatac    5280
ggcatttccc atattacacg ccatgatatg ctgcaaatcc ctgaacagca aaaaaatgaa    5340
aaatatcaag ttcctgaatt cgattcgtcc acaattaaaa atatctcttc tgcaaaaggc    5400
ctggacgttt gggacagctg gccattacaa acgctgacg gcactgtcgc aaactatcac    5460
ggctaccaca tcgtctttgc attagccgga gatcctaaaa atgcggatga cacatcgatt    5520
tacatgttct atcaaaaagt cggcgaaact tctattgaca gctggaaaaa cgctggccgc    5580
gtctttaaag acagcgacaa attcgatgca aatgattcta tcctaaaaga ccaaacacaa    5640
gaatggtcag gttcagccac atttacatct gacggaaaaa tccgtttatt ctacactgat    5700
ttctccggta acattacgg caaacaaaca ctgacaactg cacaagttaa cgtatcagca    5760
tcagacagct ctttgaacat caacggtgta gaggattata aatcaatctt tgacggtgac    5820
ggaaaaacgt atcaaaatgt acagcagttc atcgatgaag caactacag ctcaggcgac    5880 aaccatacgc tgagagatcc tcactacgta aagataaag gccacaaata cttagtattt    5940
gaagcaaaca ctggaactga agatggctac caaggcgaag aatctttatt taacaaagca    6000
tactatggca aaagcacatc attcttccgt caagaaagtc aaaaacttct gcaaagcgat    6060
aaaaaacgca cggctgagtt agcaaacggc gctctcggta tgattgagct aaacgatgat    6120
tacacactga aaaagtgat gaaccgctg attgcatcta acacagtaac agatgaaatt    6180
gaacgcgcga acgtctttaa aatgaacggc aaatggtacc tgttcactga ctcccgcgga    6240
tcaaaaatga cgattgacgg cattacgtct aacgatattt acatgcttgg ttatgtttct    6300
aattctttaa ctgcccata caagccgctg aacaaaactg gccttgtgtt aaaaatggat    6360
cttgatccta acgatgtaac ctttacttac tcacacttcg ctgtacctca agcgaaagga    6420
aacaatgtcg tgattacaag ctatatgaca aacagaggat tctacgcaga caaacaatca    6480
acgtttgcgc caagcttcct gctgaacatc aaaggcaaga aaacatctgt tgtcaaagac    6540
agcatccttg aacaaggaca attaacagtt aacaaataaa gatcctggta tgagtcagca    6600
acaccttctt cacgaggcag acctc                                          6625
```

<210> SEQ ID NO 21
<211> LENGTH: 25
<212> TYPE: DNA
<213> ORGANISM: Artificial sequence
<220> FEATURE:
<223> OTHER INFORMATION: Synthetic construct; Primer15, 5' end
      phosphorylated

<400> SEQUENCE: 21
atgaccatga ttacgaatta attcg                                          25

<210> SEQ ID NO 22
<211> LENGTH: 23
<212> TYPE: DNA
<213> ORGANISM: Artificial sequence
<220> FEATURE:
<223> OTHER INFORMATION: Synthetic construct; Primer16, 5' end
      phosphorylated

<400> SEQUENCE: 22
tcttctctca tccgccaaaa cag                                            23

<210> SEQ ID NO 23

<211> LENGTH: 10633
<212> TYPE: DNA
<213> ORGANISM: Artificial sequence
<220> FEATURE:
<223> OTHER INFORMATION: Synthetic construct; Plasmid pCRA725-SSI11-ACE

<400> SEQUENCE: 23

```
tcgacggatc gttccactga gcgtcagacc ccgtagaaaa gatcaaagga tcttcttgag      60
atccttttt  tctgcgcgta atctgctgct tgcaaacaaa aaaaccaccg ctaccagcgg     120
tggtttgttt gccggatcaa gagctaccaa ctctttttcc gaaggtaact ggcttcagca     180
gagcgcagat accaaatact gtccttctag tgtagccgta gttaggccac cacttcaaga     240
actctgtagc accgcctaca tacctcgctc tgctaatcct gttaccagtg ctgctgcca     300
gtggcgataa gtcgtgtctt accgggttgg actcaagacg atagttaccg gataaggcgc     360
agcggtcggg ctgaacgggg ggttcgtgca cacagcccag cttggagcga acgacctaca     420
ccgaactgag atacctacag cgtgagcatt gagaaagcgc cacgcttccc gaagggagaa     480
aggcggacag gtatccggta agcggcaggg tcggaacagg agagcgcacg agggagcttc     540
cagggggaaa cgcctggtat ctttatagtc ctgtcgggtt tcgccacctc tgacttgagc     600
gtcgattttt gtgatgctcg tcaggggggc ggagcctatg gaaaaacgcc agcaacgcgg     660
ccttttacg  gttcctggcc ttttgctggc cttttgctca catgttcttt cctgcgttat     720
cccctgattc tgtggataac cgtattaccg cctttgagtg agctgatacc gctcgccgca     780
gccgaacgac cgagcgcagc gagtcagtga gcgaggaagc ggaagaagct cgcacattca     840
gcagcgtttt tcagcgcgtt ttcgatcagc gtttcaatgt tggtatcaac accaggttta     900
actttgaact tatcggcact gacggttact gattttgaac ttttgctttg ccacggaacg     960
gtctgcgttg tcgggaagat gcgtgatctg atccttcaac tcagcaaaag ttcgccaata    1020
cgcaaaccgc ctctccccgc gcgttggccg attcattaat gcagctggca cgacaggttt    1080
cccgactgga aagcgggcag tgagcgcaac gcaattaatg tgagttagct cactcattag    1140
gcacccagg  ctttacactt tatgcttccg gctcgtatgt tgtgtggaat tgtgagcgga    1200
taacaatttc acacaggaaa cagctatgac catgattacg aattcgagct cggtacccgg    1260
ggatcctcta gacctcaata gagtcttcag atacaagcgc ttcactctac agcgcagtag    1320
ggttcgcgct attcggattc acttaccttg gagttgcttt gggaacctca ttatctgcag    1380
acaatcgtgg cttgggcgtt tattgtggat gggctcctgt tattgcaggc cttcttgtat    1440
atgtgaatgc cactcactc tcagatccta cactttcagt gttgtgggca tcatgggtat    1500
tactcttcgt ggctttctgt atcgccctca ctcgaaccgc aacatttggt catatgcag    1560
ccggagtctt agctgtgtac caagcattca gcaccgcaac cattcccgcg ttactattaa    1620
ttcatgagtc tccacttgca ttgattcaaa ttgcgggagc attgatctgc gtcatcgcac    1680
tattcaggcg gcagaatcag tccaagtcgc ttgaacctca acgctcatga ctcttaccga    1740
aattatccaa cgacttgtcc ccgtattggt ttttgtcgct tcaatgtctg ttgttgtaaa    1800
tctctcggcc gcagtgggtg caataacaag aatcactgaa atccttcaaa gtatcagcaa    1860
aggatctgca tggggaactt ggtggctagt catgctcata tcgaccgttt caacagtctt    1920
cttgtccttg gatacaactg ctattcttgt gactcctttg gccatagcgc tcgcggaaag    1980
agtcgggcta gctgtatttc ccttggtact cggcgtgatc tggattgcga atttaggttc    2040
cttaaccatc ccggtatcca atctgacgaa cttactctct gtatctggcg ggatgtttgt    2100
aggaacttca gactatttca gcctgtcatg gaagccagca ctcgcgacaa caatcgtagc    2160
```

```
attcgccgga ggagcaattg ctttcatttt gagaaacccc tcttcgatac acagacaatc    2220
acgtcccccg tcttctttag atacagcgca agagaattcg acatctcagg ttcattgcct    2280
agtcacatta ggtgtacttg ttccggtctt ggcatcgccg attccctatt ggatatgacc    2340
atgattacga attaattcga gctcaggcag ccatcggaag ctgtggtatg gctgtgcag     2400 gtcgtaaatc actgcataat tcgtgtcgct caaggcgcac tcccgttctg gataatgttt    2460
tttgcgccga catcataacg gttctggcaa atattctgaa atgagctgtt gacaattaat    2520
catcggctcg tataatgtgt ggaattgtga gcggataaca atttcacaca ggaaacagaa    2580
ttcccgggaa ttcaaaggag gagtgtgttg atgaaagaag ttgtaatagc tagtgcagta    2640
agaacagcga ttggatctta tggaaagtct cttaaggatg taccagcagt agatttagga    2700
gctacagcta taaggaagc agttaaaaaa gcaggaataa aaccagagga tgttaatgaa    2760
gtcattttag gaaatgttct tcaagcaggt ttaggacaga atccagcaag acaggcatct    2820
tttaaagcag gattaccagt tgaaattcca gctatgacta ttaataaggt ttgtggttca    2880
ggacttagaa cagttagctt agcagcacaa attataaaag caggagatgc tgacgtaata    2940
atagcaggtg gtatggaaaa tatgtctaga gctccttact tagcgaataa cgctagatgg    3000
ggatatagaa tgggaaacgc taaatttgtt gatgaaatga tcactgacgg attgtgggat    3060
gcatttaatg attaccacat gggaataaca gcagaaaaca tagctgagag atggaacatt    3120
tcaagagaag aacaagatga gtttgctctt gcatcacaaa aaaagctga agaagctata    3180 aaatcaggtc aatttaaaga tgaaatagtt cctgtagtaa ttaaaggcag aaagggagaa    3240
actgtagttg atacagatga gcaccctaga tttggatcaa ctatagaagg acttgcaaaa    3300
ttaaaacctg ccttcaaaaa agatggaaca gttacagctg gtaatgcatc aggattaaat    3360
gactgtgcag cagtacttgt aatcatgagt gcagaaaaag ctaaagagct tggagtaaaa    3420
ccacttgcta agatagtttc ttatggttca gcaggagttg acccagcaat aatgggatat    3480
ggacctttct atgcaacaaa agcagctatt gaaaaagcag gttggacagt tgatgaatta    3540
gatttaatag aatcaaatga agcttttgca gctcaaagtt tagcagtagc aaaagattta    3600
aaatttgata tgaataaagt aaatgtaaat ggaggagcta ttgcccttgg tcatccaatt    3660
ggagcatcag gtgcaagaat actcgttact cttgtacacg caatgcaaaa agagatgca    3720 aaaaaaggct tagcaacttt tatgtataggg ggcggacaag gaacagcaat attgctagaa    3780
aagtgctagg gatccccatc ggaagctgtg gtatggctgt gcaggtcgta aatcactgca    3840
taattcgtgt cgctcaaggc gcactcccgt tctggataat gttttttgcg ccgacatcat    3900
aacggttctg gcaaatattc tgaaatgagc tgttgacaat taatcatcgg ctcgtataat    3960
gtgtggaatt gtgagcggat aacaatttca cacaggaaac aaaggaggag tgtgttgatg    4020
aaaacaaaat tgatgacatt acaagacgcc accggcttct ttcgtgacgg catgaccatc    4080
atggtgggcg gatttatggg gattggcact ccatcccgcc tggttgaagc attactggaa    4140
tctggtgttc gcgacctgac attgatagcc aatgataccg cgtttgttga taccggcatc    4200
ggtccgctca tcgtcaatgg tcgagtccgc aaagtgattg cttcacatat cggcaccaac    4260
ccggaaacag gtcggcgcat gatatctggt gagatggacg tcgttctggt gccgcaaggt    4320
acgctaatcg agcaaattcg ctgtggtgga gctggacttg gtggttttct cacccccaacg    4380 ggtgtcggca ccgtcgtaga ggaaggcaaa cagacactga cactcgacgg taaaacctgg    4440
ctgctcgaac gcccactgcg cgccgacctg gcgctaattc gcgctcatcg ttgcgacaca    4500
cttggcaacc tgacctatca acttagcgcc cgcaacttta ccccctgat agcccttgcg    4560
```

```
gctgatatca cgctggtaga gccagatgaa ctggtcgaaa ccggcgagct gcaacctgac    4620
catattgtca ccctggtgc cgttatcgac cacatcatcg tttcacagga gagcaaataa    4680
tggatgcgaa acaacgtatt gcgcgccgtg tggcgcaaga gcttcgtgat ggtgacatcg    4740
ttaacttagg gatcggttta cccacaatgg tcgccaatta tttaccggag ggtattcata    4800
tcactctgca atcggaaaac ggcttcctcg gtttaggccc ggtcacgaca gcgcatccag    4860
atctggtgaa cgctggcggg caaccgtgcg gtgttttacc cggtgcagcc atgtttgata    4920
gcgccatgtc atttgcgcta atccgtggcg gtcatattga tgcctgcgtg ctcggcggtt    4980
tgcaagtaga cgaagaagca aacctcgcga actgggtagt gcctgggaaa atggtgcccg    5040
gtatgggtgg cgcgatggat ctggtgaccg ggtcgcgcaa agtgatcatc gccatggaac    5100
attgcgccaa agatggttca gcaaaaattt tgcgccgctg caccatgcca ctcactgcgc    5160
aacatgcggt gcatatgctg gttactgaac tggctgtctt tcgttttatt gacggcaaaa    5220
tgtggctcac cgaaattgcc gacgggtgtg atttagccac cgtgcgtgcc aaaacagaag    5280
ctcggtttga agtcgccgcc gatctgaata cgcaacgggg tgatttatga cccggggtcg    5340
acctgcagcc aagcttggct gttttggcgg atgagagaag acatgccatc ggaagctgtg    5400
gtatggctgt gcaggtcgta aatcactgca taattcgtgt cgctcaaggc gcactcccgt    5460
tctggataat gttttttgcg ccgacatcat aacggttctg gcaaatattc tgaaatgagc    5520
tgttgacaat taatcatcgg ctcgtataat gtgtggaatt gtgagcggat aacaatttca    5580
cacaggaaac aaaggaggag tgtgttgatg ttaaaggatg aagtaattaa acaaattagc    5640
acgccattaa cttcgcctgc atttcctaga ggaccctata aatttcataa tcgtgagtat    5700
tttaacattg tatatcgtac agatatggat gcacttcgta aagttgtgcc agagccttta    5760
gaaattgatg agcccttagt caggtttgaa attatggcaa tgcatgatac gagtggactt    5820
ggttgttata cagaaagcgg acaggctatt cccgtaagct ttaatggagt taagggagat    5880
tatcttcata tgatgtattt agataatgag cctgcaattg cagtaggaag ggaattaagt    5940
gcatatccta aaaagctcgg gtatccaaag cttttttgtgg attcagatac tttagtagga    6000
actttagact atggaaaact tagagttgcg acagctacaa tggggtacaa acataaagcc    6060
ttagatgcta atgaagcaaa ggatcaaatt tgtcgcccta attatatgtt gaaaataata    6120
cccaattatg atgaagccc tagaatatgt gagcttataa atgcgaaaat cacagatgtt    6180
accgtacatg aagcttggac aggaccaact cgactgcagt tatttgatca cgctatggcg    6240
ccacttaatg atttgccagt aaaagagatt gtttctagct ctcacattct tgcagatata    6300
atattgccta gagctgaagt tatatatgat tatcttaagt aaatcaagca cggtagctgc    6360
aatctatctg ctgctgattt ttagcgccag caaaagaagc cgaatcattc tttcatggac    6420
gttaatcccg tggagctccc tattctttgt ctctggacta tcacttatgg cattttttcct    6480 gcatacacaa agtgatgtca ttgcagaaga attctcatct cttttgaatt ccaccgggat    6540
ggggcctgta ttgcttaccg ccagcggtgc gatcttagcc aatttgatca acaacattcc    6600
agcttttcta gcactcgaac cagccgcaac cagcccacag agcatgatgt tcctaataat    6660
tggagtaaat gcaggcccga ttgtagcccc gtgggcttcg ctggcgactc tattgtgttt    6720
ggatcaggcc aagcgcaacg gattcaatat cccttggcgg ccaatcatcc tctgcgaat    6780 gacactttt ccttttgcta ttctcctacc tctcgccgct actttaattt gatagctcac    6840
aaggtctcta ttcatggaa atcaaaacca tcagctcgag ctaaattaac agtctgcact    6900
gcttggttac cttcaaaccg aataattccg cgtggcccctt cgaaagtcag accatcgatg    6960
```

```
atgctgttga atccttcgac tgttaagcca cgagaacgtt gagccagatg tgcaagggta    7020
taaataccct gataacaaga ctgcgccata ttgttcagcg caggggcagt tacgccggcg    7080
gtctttgaat acctacctac aaaatcaaga gcttcggggc tggttaagct ccggaagtat    7140
gaagctgagg aaaagagatt gtcggtggct tcgtagccac ttgctaacaa catattctct    7200
tccatcagcg ggctgtacct ggtgattttc tcggaaagcc cggcttcagc aaagtttctg    7260
ttgaaatcga ctgcgtcctg cccaaccaaa agcatcaaca caccatcgca accactggcg    7320
gcaacttcgc caggaagctg tggagctgcg ccttctccca tttttatgaa agagctaccc    7380
acaatatcta tgccaagcag tgaagacata gacacaatct tctcaaatga cctcaaaggc    7440
cattcatact gagcatctag agtcgacctg caggcatgca agcttggcac tggccgtcgt    7500
tttacaacgt cgtgactggg aaaaccctgg cgttacccaa cttaatcgcc ttgcagcaca    7560
tccccctttc gccagctggc gtaatagcga agaggcccgc accgatcgcc cttcccaaca    7620
gttgcgcagc ctgaatggcg aatgcgattt attcaacaaa gccgccgtcc cgtcaagtca    7680
gcgtaatgct ctgccagtgt acaaccaat taaccaattc tgattagaaa aactcatcga    7740
gcatcaaatg aaactgcaat ttattctatat caggattatc aataccatat ttttgaaaaa    7800
gccgtttctg taatgaagga gaaaactcac cgaggcagtt ccataggatg caagatcct    7860
ggtatcggtc tgcgattccg actcgtccaa catcaataca acctattaat ttcccctcgt    7920
caaaaataag gttatcaagt gagaaatcac catgagtgac gactgaatcc ggtgagaatg    7980
gcaaaagctt atgcatttct ttccagactt gttcaacagg ccagccatta cgctcgtcat    8040
caaaatcact cgcatcaacc aaaccgttat tcattcgtga ttgcgcctga gcgagacgaa    8100
atacgcgatc gctgttaaaa ggacaattac aaacaggaat cgaatgcaac cggcgcagga    8160
acactgccag cgcatcaaca atattttcac ctgaatcagg atattcttct aatacctgga    8220
atgctgtttt cccggggatc gcagtggtga gtaaccatgc atcatcagga gtacggataa    8280
aatgcttgat ggtcggaaga ggcataaatt ccgtcagcca gtttagtctg accatctcat    8340
ctgtaacatc attggcaacg ctaccttgc catgtttcag aaacaactct ggcgcatcgg    8400
gcttcccata caatcgatag attgtcgcac ctgattgccc gacattatcg cgagcccatt    8460
tatacccata taaatcagca tccatgttgg aatttaatcg cggcttcgag caagacgttt    8520
cccgttgaat atggctcata caccccttg tattactgtt tatgtaagca gacagtttta    8580
ttgttcatga tgatatattt ttatcttgtg caatgtaaca tcagagattt tgagacacaa    8640
cgtggctttg ttgaataaat cgaacttttg ctgagttgaa ggatcagatc acgcatcttc    8700
ccgacaacgc agaccgttcc gtggcaaagc aaaagttcaa aatcaccaac tggtccacct    8760
acaacaaagc tctcatcaac cgtggctccc tcactttctg gctggatgat ggggcgattc    8820
aggatccata ttcgtgtcg ctcaaggcgc actcccgttc tggataatgt ttttgcgcc    8880
gacatcataa cggttctggc aaatattctg aaatgagctg ttgacaatta atcatcggct    8940
cgtataatgt gtggaattgt gagcggataa caatttcaca caggaaacag aattgataaa    9000
gcaggcaaga cctaaaatgt gtaaagggca aagtgtatac tttggcgtca ccccttacat    9060
attttaggtc ttttttttatt gtgcgtaact aacttgccat cttcaaacag gagggctgga    9120
agaagcagac cgctaacaca gtacataaaa aaggagacat gaacgatgaa catcaaaaag    9180
tttgcaaaac aagcaacagt attaacccttt actaccgcac tgctggcagg aggcgcaact    9240
caagcgtttg cgaagaaaac gaaccaaaag ccatataagg aaacatacgg catttcccat    9300
attacacgcc atgatatgct gcaaatccct gaacagcaaa aaaatgaaaa atatcaagtt    9360
```

```
cctgaattcg attcgtccac aattaaaaat atctcttctg caaaaggcct ggacgtttgg    9420
gacagctggc cattacaaaa cgctgacggc actgtcgcaa actatcacgg ctaccacatc    9480
gtctttgcat tagccggaga tcctaaaaat gcggatgaca catcgattta catgttctat    9540
caaaaagtcg gcgaaacttc tattgacagc tggaaaaacg ctggccgcgt ctttaaagac    9600
agcgacaaat tcgatgcaaa tgattctatc ctaaaagacc aaacacaaga atggtcaggt    9660
tcagccacat ttacatctga cggaaaaaat cgtttattct acactgattt ctccggtaaa    9720
cattacggca acaaacact  gacaactgca caagttaacg tatcagcatc agacagctct    9780
ttgaacatca acggtgtaga ggattataaa tcaatctttg acggtgacgg aaaaacgtat    9840
caaaatgtac agcagttcat cgatgaaggc aactacagct caggcgacaa ccatacgctg    9900
agagatcctc actacgtaga agataaaggc cacaaatact tagtatttga agcaaacact    9960
ggaactgaag atggctacca aggcgaagaa tctttatta  acaaagcata ctatggcaaa   10020
agcacatcat tcttccgtca agaaagtcaa aaacttctgc aaagcgataa aaaacgcacg   10080
gctgagttag caaacggcgc tctcggtatg attgagctaa cgatgatta  cacactgaaa   10140
aaagtgatga accgctgat  tgcatctaac acagtaacag atgaaattga acgcgcgaac   10200
gtctttaaaa tgaacggcaa atggtacctg ttcactgact cccgcggatc aaaaatgacg   10260
attgacggca ttacgtctaa cgatatttac atgcttggtt atgtttctaa ttctttaact   10320
ggcccataca agccgctgaa caaaactggc cttgtgttaa aatggatct  tgatcctaac   10380
gatgtaacct ttacttactc acacttcgct gtacctcaag cgaaaggaaa caatgtcgtg   10440
attacaagct atatgacaaa cagaggattc tacgcagaca aacaatcaac gtttgcgcca   10500
agcttcctgc tgaacatcaa aggcaagaaa acatctgttg tcaaagacag catccttgaa   10560
caaggacaat taacagttaa caaataaaga tcctggtatg agtcagcaac accttcttca   10620
cgaggcagac ctc                                                      10633

<210> SEQ ID NO 24
<211> LENGTH: 5302
<212> TYPE: DNA
<213> ORGANISM: Artificial sequence
<220> FEATURE:
<223> OTHER INFORMATION: Synthetic construct; Plasmid pCRC204

<400> SEQUENCE: 24
atgaccatga ttacgaattc ggctgtgcag gtcgtaaatc actgcataat tcgtgtcgct     60
caaggcgcac tcccgttctg gataatgttt tttgcgccga catcataacg gttctggcaa    120
atattctgaa atgagctgtt gacaattaat catcggctcg tataatgtgt ggaattgtga    180
gcggataaca atttcacaca ggaaacaaag gaggagtgtg ttgatgaaag ccgtccagta    240
caccgagatc ggctccgagc cggtcgttgt cgacatcccc accccgacgc ccgggccggg    300
tgagatcctg ctgaaggtca ccgcggccgg gctgtgccac tcggacatct tcgtgatgga    360
catgccggcg gcgcagtacg cctacggcct gccgctcacc ctcggccacg agggtgtcgg    420
caccgtcgcc gaactcggcg agggcgtcac gggattcggg gtgggggacg ccgtcgccgt    480
gtacgggccg tggggctgcg gtgcgtgcca cgcctgcgcg cgcggccggg agaactactg    540
cacccgcgcc gccgacctgg gcatcacgcc accggtctc  ggctcgcccg gatcgatggc    600
cgagtacatg atcgtcgatt cggcgcgcca cctcgtcccg atcggagacc tcgacccggt    660
cgccgcggcg ccgctcaccg acgccggtct gacgccgtac cacgcgatct cccgggtcct    720
gccgctgctg gggccgggct cgacggccgt cgtcatcggt gtcggcggc  tcggccacgt    780
```

```
cggcatccag atcctgcgcg ccgtcagcgc ggcccgtgtg atcgccgtcg acctcgacga    840
cgaccgtctc gccctcgccc gcgaggtcgg cgccgacgcg gcggtgaagt cgggcgccgg    900
tgcggcggac gcgatccggg aactgaccgg cggccagggc gcgacggcgg tgttcgactt    960
cgtcggcgcc cagtcgacga tcgacacggc gcagcaggtg gtcgcggtcg acgggcacat   1020
ctcggtcgtg ggcatccacg ccggcgcaca cgccaaggtc gggttcttca tgatcccgtt   1080
cggcgcctcc gtcgtgaccc cgtactgggg caccccggtcg gaactgatgg aggtcgtcgc   1140
gctggcccgc gccggccggc tggacatcca caccgagacg ttcaccctcg acgaggggcc   1200
ggcggcgtac cggcggctgc gcgagggcag catccgcggc cgcggcgtgg tggttccctg   1260
atatcgaatt cgagctcggt acccggggat cctctagagt cgacctgcag gcatgcaagc   1320
ttggcactgg ccgtcgtttt acaacgtcgt gactgggaaa accctggcgt tacccaactt   1380
aatcgccttg cagcacatcc ccctttcgcc agctggcgta atagcgaaga ggcccgcacc   1440
gatcgccctt cccaacagtt gcgcagcctg aatggcgaat gagcttcttc cgcttcctcg   1500
ctcactgact cgctgcgctc ggtcgttcgg ctgcggcgag cggtatcagc tcactcaaag   1560
gcggtaatac ggttatccac agaatcaggg gataacgcag gaaagaacat gtgagcaaaa   1620
ggccagcaaa aggccaggaa ccgtaaaaag gccgcgttgc tggcgttttt ccataggctc   1680
cgcccccctg acgagcatca caaaaatcga cgctcaagtc agaggtggcg aaacccgaca   1740
ggactataaa gataccaggc gtttccccct ggaagctccc tcgtgcgctc tcctgttccg   1800
accctgccgc ttaccggata cctgtccgcc tttctccctt cgggaagcgt ggcgctttct   1860
caatgctcac gctgtaggta tctcagttcg gtgtaggtcg ttcgctccaa gctgggctgt   1920
gtgcacgaac cccccgttca gcccgaccgc tgcgccttat ccggtaacta tcgtcttgag   1980
tccaacccgg taagacacga cttatcgcca ctggcagcag ccactggtaa caggattagc   2040
agagcgaggt atgtaggcgg tgctacagag ttcttgaagt ggtggcctaa ctacggctac   2100
actagaagga cagtatttgg tatctgcgct ctgctgaagc cagttacctt cggaaaaaga   2160
gttggtagct cttgatccgg caaacaaacc accgctggta gcggtggttt ttttgtttgc   2220
aagcagcaga ttacgcgcag aaaaaaagga tctcaagaag atcctttgat cttttctacg   2280
gggtctgacg ctcagtggaa cgataacaca tgcagtcatg tcgtgctaat gtgtaaaaca   2340
tgtacatgca gattgctggg ggtgcagggg gcggagccac cctgtccatg cggggtgtgg   2400
ggcttgcccc gccggtacag acagtgagca ccggggcacc tagtcgcgga tacccccct   2460
aggtatcgga cacgtaaccc tcccatgtcg atgcaaatct ttaacattga gtacgggtaa   2520
gctggcacgc atagccaagc taggcggcca ccaaacacca ctaaaaatta atagtcccta   2580
gacaagacaa accccgtgc gagctaccaa ctcatatgca cggggccac ataacccgaa   2640
ggggtttcaa ttgacaacca tagcactagc taagacaacg ggcacaacac ccgcacaaac   2700
tcgcactgcg caaccccgca caacatcggg tctaggtaac actgaaatag aagtgaacac   2760
ctctaaggaa ccgcaggtca atgagggttc taaggtcact cgcgctaggg cgtggcgtag   2820
gcaaaacgtc atgtacaaga tcaccaatag taaggctctg gcggggtgcc ataggtggcg   2880
cagggacgaa gctgttgcgg tgtcctggtc gtctaacggt gcttcgcagt ttgagggtct   2940
gcaaaactct cactctcgct gggggtcacc tctggctgaa ttggaagtca tgggcgaacg   3000
ccgcattgag ctggctattg ctactaagaa tcacttggcg gcgggtggcg cgctcatgat   3060
gtttgtgggc actgttcgac acaaccgctc acagtcattt gcgcaggttg aagcgggtat   3120
taagactgcg tactcttcga tggtgaaaac atctcagtgg aagaaagaac gtgcacggta   3180
```

-continued

```
cggggtggag cacacctata gtgactatga ggtcacagac tcttgggcga acggttggca    3240
cttgcaccgc aacatgctgt tgttcttgga tcgtccactg tctgacgatg aactcaaggc    3300
gtttgaggat tccatgtttt cccgctggtc tgctggtgtg gttaaggccg gtatggacgc    3360
gccactgcgt gagcacgggg tcaaacttga tcaggtgtct acctggggtg gagacgctgc    3420
gaaaatggca acctacctcg ctaagggcat gtctcaggaa ctgactggct ccgctactaa    3480
aaccgcgtct aaggggtcgt acacgccgtt tcagatgttg gatatgttgg ccgatcaaag    3540
cgacgccggc gaggatatgg acgctgtttt ggtggctcgg tggcgtgagt atgaggttgg    3600
ttctaaaaac ctgcgttcgt cctggtcacg tgggctaag cgtgctttgg gcattgatta    3660
catagacgct gatgtacgtc gtgaaatgga agaagaactg tacaagctcg ccggtctgga    3720
agcaccggaa cgggtcgaat caacccgcgt tgctgttgct ttggtgaagc ccgatgattg    3780
gaaactgatt cagtctgatt cgcggttag gcagtacgtt ctagattgcg tggataaggc    3840
taaggacgtg gccgctgcgc aacgtgtcgc taatgaggtg ctggcaagtc tgggtgtgga    3900
ttccaccccg tgcatgatcg ttatggatga tgtggacttg gacgcggttc tgcctactca    3960
tggggacgct actaagcgtg atctgaatgc ggcggtgttc gcgggtaatg agcagactat    4020
tcttcgcacc cactaaaagc ggcataaacc ccgttcgata ttttgtgcga tgaatttatg    4080
gtcaatgtcg cgggggcaaa ctatgatggg tcttgttgtg ttatctccgt cgaacggaag    4140
atcacttcgc agaataaata aatcctggtg tccctgttga taccgggaag ccctgggcca    4200
acttttggcg aaaatgagac gttgatcggc acgtaagagg ttccaacttt caccataatg    4260
aaataagatc actaccgggc gtattttttg agttatcgag attttcagga gctaaggaag    4320
ctaaaatgga gaaaaaatc actggatata ccaccgttga tatatcccaa tggcatcgta    4380
aagaacattt tgaggcattt cagtcagttg ctcaatgtac ctataaccag accgttcagc    4440
tggatattac ggcctttta aagaccgtaa agaaaaataa gcacaagttt tatccggcct    4500
ttattcacat tcttgcccgc ctgatgaatg ctcatccgga atttcgtatg gcaatgaaag    4560
acggtgagct ggtgatatgg gatagtgttc acccttgtta caccgttttc catgagcaaa    4620
ctgaaacgtt ttcatcgctc tggagtgaat accacgacga tttccggcag tttctacaca    4680
tatattcgca agatgtggcg tgttacggtg aaaacctggc ctatttccct aaagggttta    4740
ttgagaatat gttttcgtc tcagccaatc cctgggtgag tttcaccagt tttgatttaa    4800
acgtggccaa tatggacaac ttcttcgccc ccgttttcac catgggcaaa tattatacgc    4860
aaggcgacaa ggtgctgatg ccgctggcga ttcaggttca tcatgccgtc tgtgatggct    4920
tccatgtcgg cagaatgctt aatgaattac aacagtactg cgatgagtgg cagggcgggg    4980
cgtaattttt ttaaggcagt tattggtgcc cttaaacgcc tggtgctacg cctgaataag    5040
tgataataag cggatgaatg gcagaaattc agcttggccc agtgccaagc tccaatacgc    5100
aaaccgcctc tccccgcgcg ttggccgatt cattaatgca gctggcacga caggtttccc    5160
gactggaaag cgggcagtga gcgcaacgca attaatgtga gttagctcac tcattaggca    5220
ccccaggctt tacactttat gcttccggct cgtatgttgt gtggaattgt gagcggataa    5280
caatttcaca caggaaacag ct                                             5302
```

TRANSFORMANT OF CORYNEFORM BACTERIA CAPABLE OF PRODUCING ISOPROPANOL

This application is a U.S. national stage of International Application No. PCT/JP2009/057547 filed Apr. 15, 2009.

TECHNICAL FIELD

The present invention relates to technology for producing isopropanol. In more detail, the present invention relates to a transformant of a coryneform bacterium in which specific gene manipulation to provide an isopropanol producing ability was performed, and relates to an efficient isopropanol producing technology using the same.

BACKGROUND ART

Isopropanol, as an industrial solvent for paints, inks, or the like, or as an industrial raw material for various uses, is currently produced in an amount of about 1,800,000 tons per year worldwide and about 180,000 tons per year in Japan. Also, isopropanol can be converted into propylene by a simple dehydration reaction, and therefore can be used as a source of polypropylene, which is currently produced in an amount of about 3,100,000 tons per year in Japan.

However, these products are all derived from fossil crude resources.

Development of new methods for producing energy or chemical products not from fossil resources, almost all of which are imported, but from renewable resources is strongly desired in order to solve global environmental issues such as global warming, exhaustion of fossil resources, and soaring oil prices, and to reduce the dependence on foreign countries for important raw material resources of chemical products. Efficient technology for producing isopropanol from renewable resources, such as biomass, would be one of the measures to solve these problems.

As an example of microbial production of isopropanol from biomass resources, it is reported that a kind of *Clostridium* that performs acetone-butanol fermentation produces isopropanol in addition to butanol (isopropanol-butanol fermentation). This is because the *Clostridium* exhibiting such a fermentation pattern has isopropanol dehydrogenase, which reduces acetone to isopropanol as a catalyst.

In recent years, the production and use of biofuel is increasing around the world, and from the standpoint of biofuel production, researches on butanol production based on acetone-butanol fermentation are attracting attention again. However, these researches are primarily intended for butanol production, and few of them are intended for isopropanol production.

As bacteria which produce isopropanol, *Clostridium* bacteria known as isopropanol-butanol fermenting bacteria, such as *Clostridium beijerinckii*, *Clostridium aurantibutyricum*, etc. have been reported so far (Applied and Environmental Microbiology, Vol. 45, 1983, 1160-1163).

However, isopropanol production using *Clostridium* bacteria has the following problems.

(1) In isopropanol-butanol fermentation by *Clostridium* bacteria, butanol is the main fermentation metabolite, and isopropanol is produced in low efficiency. (The ratio of isopropanol/butanol to be produced is about ⅕ to ¹/₁₀.)

(2) *Clostridium* bacteria require strictly anaerobic conditions in proliferation and in production of isopropanol. Therefore, for such strictly anaerobic conditions, complicated culture procedure involving, for example, replacement of the air in the culture apparatus with an inert gas such as nitrogen gas, is required. In addition, the proliferation rate is extremely low, and as a result, the isopropanol production rate is low. To solve these problems, use of aerobic bacteria with a high proliferation rate may be considered, but no microorganism (an aerobic bacterium or a facultative anaerobic bacterium) capable of producing isopropanol with high efficiency and proliferating under aerobic conditions has yet been known.

(3) In isopropanol-butanol fermentation, acetic acid and butyric acid are generated during cell-growth phase, and during stationary phase, in which cell growth stops, acidification to lower pH in fermentation culture triggers transition to solvent (isopropanol and butanol)-production phase, resulting in a drastic change in metabolic system (catabolic shift) and production of isopropanol and butanol. Thus, fermentation process must be strictly controlled, and substantial time is required from the start of fermentation to production of isopropanol and butanol. Also, these *Clostridium* bacteria have problems including that transition to sporulation phase stops the production of isopropanol and butanol, that is, the production of isopropanol does not last long.

To solve these problems, inventions of a novel isopropanol-producing microorganism and a novel isopropanol-producing process have been desired.

For producing isopropanol with the use of *Clostridium* bacteria, the following techniques have been disclosed.

Applied and Environmental Microbiology, Vol. 45, 1983, 1160-1163 discloses that *Clostridium beijerinckii* produces isopropanol in addition to butanol and that *Clostridium aurantibutyricum* produces isopropanol in addition to butanol and acetone.

Also, Enzyme and Microbial Technology, Vol. 5, 1983, 46-54 and Biotechnology and Bioengineering, Vol. 39, 1992, 148-156 disclose a continuous isopropanol-producing technique using immobilized *Clostridium* bacteria; Applied Microbiology and Biotechnology, Vol. 32, 1989, 22-26 discloses an isopropanol-producing technique using agglutinating *Clostridium* bacteria; Applied Microbiology and Biotechnology, Vol. 25, 1986, 29-31 discloses a technique of catabolite repression in isopropanol-butanol fermentation mediated by *Clostridium* bacteria, by adding a polymer resin to adsorb catabolites, which are isopropanol and butanol. However, the focus of these techniques is producing butanol, and they are all isopropanol-producing techniques using *Clostridium* bacteria under anaerobic conditions. Therefore, they are not fundamental solutions to the problems pointed out in the above (1), (2), (3), etc.

Meanwhile, although not for isopropanol production, the following acetone-butanol producing techniques using *Clostridium* bacteria have been disclosed so far.

WO 2006/007530 discloses a technique of controlling a gene responsible for sporulation to delay sporulation phase for increasing butanol production; US 2005/089979 A1 and Bioprocess and Biosystems Engineering, Vol. 27, 2005, 207-214 disclose a technique of continuous extraction of butanol by the gas-stripping method in continuous fermentation; Pakistan Journal of Biological Sciences, Vol. 9, 2006, 1923-1928 and Applied Biochemistry and Biotechnology, Vol. 113-116, 2004, 887-898 disclose a butanol-producing technique by immobilizing *Clostridium* bacteria; Journal of Biotechnology, Vol. 120, p 197-206 discloses a technique of recycling bacteria cells in continuous fermentation by using high-density *Clostridium* bacteria. Although these techniques are considered to be applicable to isopropanol-butanol fermentation as well using *Clostridium* bacteria, they are nothing but production techniques using *Clostridium* bacteria under anaerobic conditions, and therefore not fundamental solutions to the above-mentioned problems.

Examples of techniques for producing isopropanol with the use of bacteria other than *Clostridium* bacteria include the following.

The inventors have already proposed a technique for producing isopropanol with the use of *Escherichia coli* as a host (JP 2007-222633 A and Applied Microbiology and Biotechnology, Vol. 77, 2008, 1219-1224). Applied and Environmental Microbiology, Vol. 73, 2007, 7814-7818 discloses a technique for producing isopropanol by expressing genes which encode acetyl-CoA acetyltransferase, acetoacetyl-CoA:acetate-CoA transferase, acetoacetate decarboxylase, and isopropanol dehydrogenase derived from a microorganism selected from *Clostridium acetobutylicum*, *Escherichia coli*, *Clostridium beijerinckii*, and *Thermoanaerobacter brockii*, in *Escherichia coli* as a host.

However, the above-mentioned techniques have room for improvement to produce isopropanol with the use of a microorganism more efficiently.

SUMMARY OF INVENTION

Technical Problem

An object of the present invention is to provide a recombinant microorganism capable of producing isopropanol, from renewable resources, and a method for efficiently producing isopropanol using the microorganism.

Solution to Problem

The present inventors made extensive examination to solve the problem described above, and found that isopropanol is efficiently produced by transformants created by transferring an exogenous gene which encodes an enzyme having acetyl-CoA acetyltransferase activity, an exogenous gene which encodes an enzyme having acetoacetyl-CoA:acetate CoA-transferase activity, an exogenous gene which encodes an enzyme having acetoacetate decarboxylase activity, and an exogenous gene which encodes an enzyme having isopropanol dehydrogenase activity, into a coryneform bacterium.

The technology of the present invention which uses a coryneform bacterium as a host is superior to techniques which use *Escherichia coli* as a host in several points.

While *Escherichia coli* cannot proliferate in the presence of 3.5% isopropanol, a coryneform bacterium can proliferate even in the presence of 5% isopropanol, and therefore a coryneform bacterium has a higher resistance to isopropanol as compared with *Escherichia coli* (see the Examples described below). This indicates that a coryneform bacterium is superior to *Escherichia coli* as a host in production of a high concentration of isopropanol. That is, the technology of the present invention is industrially advantageous because production of a high concentration of isopropanol requires less energy to collect and purify isopropanol from a fermentation broth.

The inventors have already disclosed a technique in which a recombinant *Corynebacterium glutamicum* is made to react in a reaction mixture under reducing conditions, where proliferation is inhibited, for highly efficient production of lactic acid, succinic acid, or ethanol (JP 3869788).

The inventors newly found out that the recombinant coryneform bacterium of the present invention efficiently produces isopropanol under conditions where proliferation is inhibited (see the Examples described below).

This fact means that the carbonaceous flow is solely used for production of the objective product, not used for proliferation. It also means that substantial inhibition of the secretions accompanying proliferation and cell division is achieved. This also contributes to high efficiency and low energy consumption in the collection and purification of isopropanol in the method of the present invention.

Therefore, providing, by genetic recombination, a coryneform bacterium with capability of producing isopropanol is a more efficient technique than an isopropanol producing technique involving proliferation of recombinant *Escherichia coli*, or the like.

The present invention, which has been completed based on the above-mentioned findings, provides the following microorganism and a method for producing isopropanol using the microorganism.

(1) A transformant capable of producing isopropanol, which is constructed by transferring the following genes (a) to (d) into a coryneform bacterium:
(a) an exogenous gene which encodes an enzyme having acetyl-CoA acetyltransferase activity;
(b) an exogenous gene which encodes an enzyme having acetoacetyl CoA:acetate CoA-transferase activity;
(c) an exogenous gene which encodes an enzyme having acetoacetate decarboxylase activity; and
(d) an exogenous gene which encodes an enzyme having isopropanol dehydrogenase activity.

(2) The transformant according to the above (1), wherein
(a) the exogenous gene which encodes an enzyme having acetyl-CoA acetyltransferase activity is a DNA comprising the base sequence of SEQ ID NO: 13, or a DNA which hybridizes to a DNA comprising a complementary base sequence of a DNA comprising the base sequence of SEQ ID NO: 13 under stringent conditions and which encodes a polypeptide having acetyl-CoA acetyltransferase activity;
(b) the exogenous gene which encodes an enzyme having acetoacetyl CoA:acetate CoA-transferase activity is a DNA comprising the base sequence of SEQ ID NO: 14, or a DNA which hybridizes to a DNA comprising a complementary base sequence of a DNA comprising the base sequence of SEQ ID NO: 14 under stringent conditions and which encodes a polypeptide having acetoacetyl CoA:acetate CoA-transferase activity;
(c) the exogenous gene which encodes an enzyme having acetoacetate decarboxylase activity is a DNA comprising the base sequence of SEQ ID NO: 15, or a DNA which hybridizes to a DNA comprising a complementary base sequence of a DNA comprising the base sequence of SEQ ID NO: 15 under stringent conditions and which encodes a polypeptide having acetoacetate decarboxylase activity; and
(d) the exogenous gene which encodes an enzyme having isopropanol dehydrogenase activity is a DNA comprising the base sequence of SEQ ID NO: 16, or a DNA which hybridizes to a DNA comprising a complementary base sequence of a DNA comprising the base sequence of SEQ ID NO: 16 under stringent conditions and which encodes a polypeptide having isopropanol dehydrogenase activity.

(3) The transformant according to the above (1) or (2), wherein
(a) the exogenous gene which encodes an enzyme having acetyl-CoA acetyltransferase activity, (b) the exogenous gene which encodes an enzyme having acetoacetyl CoA:acetate CoA-transferase activity, (c) the exogenous gene which encodes an enzyme having acetoacetate decarboxylase activity, and (d) the exogenous gene which encodes an enzyme having isopropanol dehydrogenase activity are genes derived from a same or different microorganism selected from the group consisting of *Clostridium acetobutylicum, Escherichia coli, Rhodococcus ruber, Clostridium beijerinckii, Clostridium aurantibutyricum, Clostridium saccharoperbutylacetonicum, Clostridium saccharoacetobutylicum, Clostridium pasteurianum, Clostridium sporogenes, Clostridium cadaveris, Clostridium tetanomorphum,* and *Ralstonia eutropha.*

(4) The transformant according to any of the above (1) to (3), wherein (b) the exogenous gene which encodes an enzyme having acetoacetyl CoA:acetate CoA-transferase activity is a gene derived from *Escherichia coli,* and/or (d) the exogenous gene which encodes an enzyme having isopropanol dehydrogenase activity is a gene derived from *Rhodococcus ruber.*

(5) The transformant according to any of the above (1) to (4), wherein the coryneform bacterium is selected from the group consisting of *Corynebacterium, Brevibacterium,* and *Arthrobacter.*

(6) A transformant, which is *Corynebacterium glutamicum* ISO1 (Accession Number: NITE BP-561), or *Corynebacterium glutamicum* ISO2 (Accession Number: NITE BP-562).

(7) A method for producing isopropanol, which comprises a step of culturing the transformant according to any one of the above (1) to (6) in a culture medium containing saccharides, and a step of collecting isopropanol from a resulting culture.

Advantageous Effects of Invention

The transformant of the present invention is capable of extremely efficient production of isopropanol from saccharides.

The present invention enables efficient isopropanol production from renewable resources and construction of a new process for industrially producing isopropanol without depending on petroleum resources.

DESCRIPTION OF EMBODIMENTS

Figure 1:
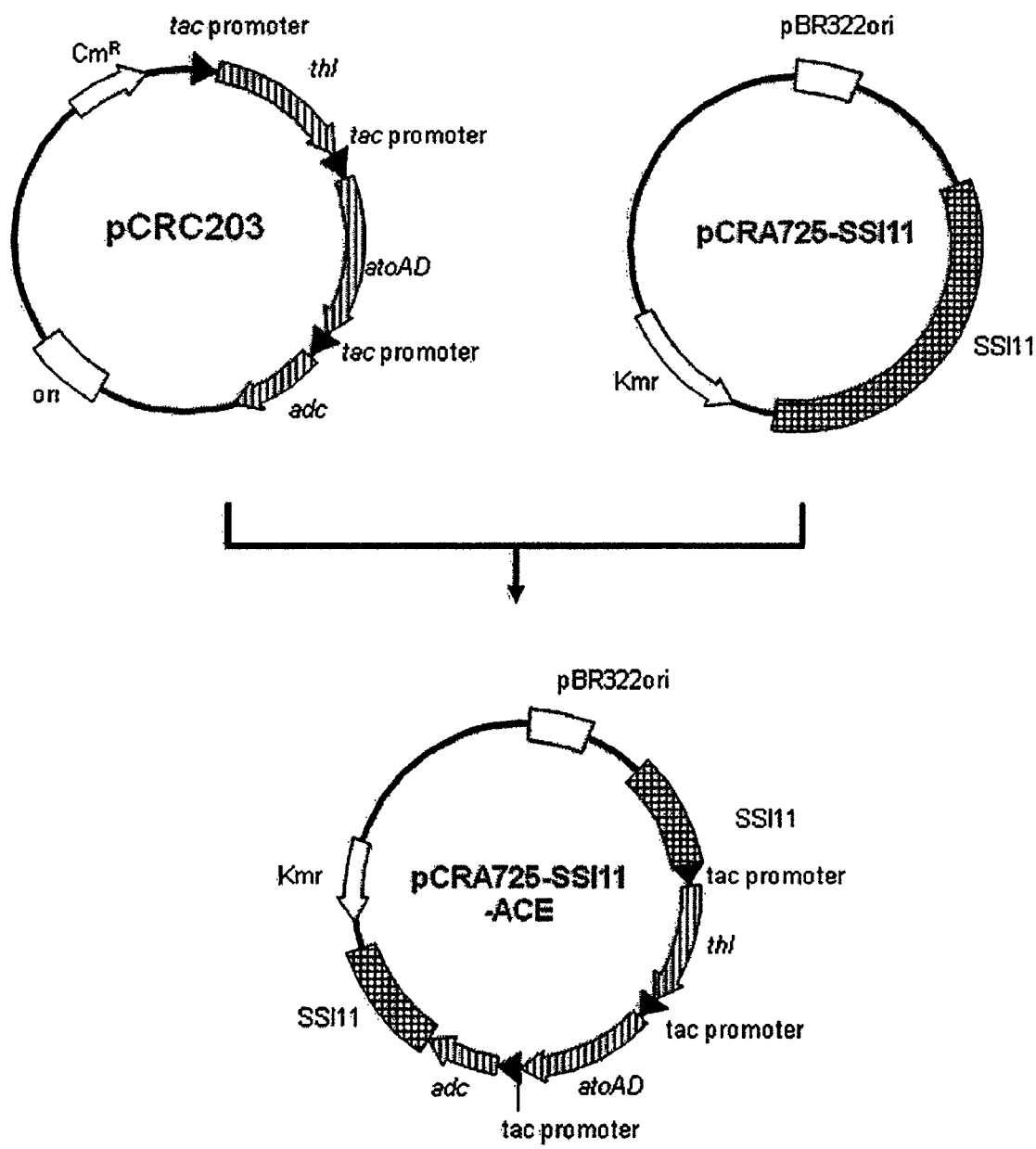
FIG. 1 is a schematic view showing a method for preparing the plasmid pCRA725-SSI11-ACE prepared in Example 1 (2).

Hereinafter, the present invention will be described in detail.

(I) Transformant Capable of Producing Isopropanol

The transformant of the present invention capable of producing isopropanol is a transformant which is constructed by transferring the following genes (a) to (d) into a coryneform bacterium:

(a) an exogenous gene which encodes an enzyme having acetyl-CoA acetyltransferase activity;
(b) an exogenous gene which encodes an enzyme having acetoacetyl CoA:acetate CoA-transferase activity;
(c) an exogenous gene which encodes an enzyme having acetoacetate decarboxylase activity; and
(d) an exogenous gene which encodes an enzyme having isopropanol dehydrogenase activity.

Host

The host subjected to transformation in the present invention is not particularly limited as long as it is a coryneform bacterium capable of being transformed by a recombinant vector comprising a group of isopropanol production-related genes, allowing expression of isopropanol production-related enzymes encoded by the genes, and producing isopropanol as a result.

The coryneform bacteria is a group of microorganisms defined in Bargeys Manual of Determinative Bacteriology, Vol. 8, 599 (1974), and is not particularly limited as long as it proliferates under normal aerobic conditions. The specific examples include *Corynebacterium, Brevibacterium, Arthrobacter, Mycobacterium* and *Micrococcus.*

Further specifically, examples of the *Corynebacterium* in the coryneform bacteria include *Corynebacterium glutamicum* R (FERM P-18976), ATCC13032, ATCC13058, ATCC13059, ATCC13060, ATCC13232, ATCC13286, ATCC13287, ATCC13655, ATCC13745, ATCC13746, ATCC13761, ATCC14020 and ATCC31831.

Examples of the *Brevibacterium* include *Brevibacterium lactofermentum* ATCC13869; *Brevibacterium flavum* MJ-233 (FERM BP-1497) and MJ-233AB-41 (FERM BP-1498); and *Brevibacterium ammoniagenes* ATCC6872.

Examples of the *Arthrobacter* include *Arthrobacter globiformis* ATCC8010, ATCC4336, ATCC21056, ATCC31250, ATCC31738 and ATCC35698.

Examples of the *Mycobacterium* include *Mycobacterium bovis* ATCC19210 and ATCC27289.

Examples of the *Micrococcus* include *Micrococcus freudenreichii* NO. 239 (FERM P-13221), *Micrococcus leuteus* NO. 240 (FERM P-13222), *Micrococcus ureae* IAM1010, and *Micrococcus roseus* IFO3764.

The coryneform bacteria may be, let alone a wild strain, a mutant thereof or an artificial recombinant thereof. Examples of such coryneform bacteria include disruptants of the respective genes encoding lactate dehydrogenase, phosphoenolpyruvate carboxylase, and malate dehydrogenase.

As a coryneform bacterium which serves as a host in the present invention, *Corynebacterium* is preferred and *Corynebacterium glutamicum* R (FERM P-18976) is particularly preferred.

Isopropanol Production-Related Genes

As the above (a) to (d) isopropanol production-related genes, when the base sequences of DNA fragments comprising these genes are known, DNA fragments synthesized according to the sequences may be used. Even when the DNA sequences are unknown, necessary fragments can be obtained by a hybridization method and the PCR method based on amino acid sequences conserved among isopropanol production-related enzyme proteins. Also, such fragments can be obtained by degenerate PCR using mixed primers designed based on other known isopropanol production-related gene sequences.

In the above (a) to (d) isopropanol production-related genes, as long as their isopropanol-producing activity is maintained, a part of the base sequence may be substituted or deleted. Also, a base may be newly inserted, and a part of the base sequence may be transposed. Any of these derivatives may be used in the present invention. The above-mentioned "a part" may be, for example, one to several (usually 1 to 5, preferably 1 to 3, and more preferably 1 to 2) in terms of amino-acid residues.

An isopropanol-producing bacterium usually carries the above (a) to (d) genes. Examples of the isopropanol-producing bacterium include *Clostridium* bacteria known to perform butanol-isopropanol fermentation, such as *Clostridium beijerinckii* and *Clostridium aurantibutyricum* (George, H. A. et al., Acetone, Isopropanol, and Butanol Production by *Clostridium beijerinckii* (syn. *Clostridium butylicum*) and *Clostridium aurantibutyricum.* Appl. Environ. Microbiol.

45:1160-1163 (1983)), and it has already been reported that isopropanol is produced from acetyl-CoA through a 4-step reaction (Mitchell, W. J., Physiology of carbohydrate to solvent conversion by clostridia. Adv. Microb. Physiol. 39:31-130 (1998)).

In particular, the isopropanol-producing pathway or the metabolic pathway from acetyl-CoA to isopropanol in the above *Clostridium* bacteria involves acetyl-CoA acetyltransferase (also known as thiolase) (hereinafter the gene and the enzyme will be abbreviated to "thl" and "THL", respectively) that catalyzes the reaction from acetyl-CoA to acetoacetyl-CoA, acetoacetyl CoA:acetate CoA transferase (hereafter the gene and the enzyme will be abbreviated to "atoAD" and "CTF", respectively) that catalyzes the reaction from acetoacetyl-CoA to acetoacetate, acetoacetate decarboxylase (hereafter the gene and the enzyme will be abbreviated to "adc" and "ADC", respectively) that catalyzes the reaction from acetoacetate to acetone, and isopropanol dehydrogenase (also known as primary-secondary alcohol dehydrogenase) (hereafter the gene and the enzyme will be abbreviated to "adh" and "ADH", respectively) that catalyzes the reaction from acetone to isopropanol.

The present invention uses this metabolic system. The species and combination of the microorganism of origin, the order of transfer, etc. of the above (a) to (d) genes are not limited as long as the isopropanol-producing ability is maintained.

The above (a) to (d) genes may be obtained from bacteria incapable of producing isopropanol. The specific examples include the following.

As *Clostridium* bacteria which do not produce isopropanol but perform butanol-acetone fermentation, *Clostridium acetobutylicum, Clostridium saccharoperbutylacetonicum, Clostridium saccharoacetobutylicum, Clostridium pasteurianum, Clostridium sporogenes, Clostridium cadaveris, Clostridium tetanomorphum*, etc. have been reported (George, H. A. et al., Acetone, Isopropanol, and Butanol Production by *Clostridium beijerinckii* (syn. *Clostridium butylicum*) and *Clostridium aurantibutyricum*. Appl. Environ. Microbiol. 45:1160-1163 (1983)). It has been reported that these *Clostridium* bacteria which perform butanol-acetone fermentation have the genes which encode enzymes for the three steps from acetyl-CoA to acetone (THL, CTF and ADC) for acetone production (Nolling, J. et al., Genome sequence and comparative analysis of the solvent-producing bacterium *Clostridium acetobutylicum*. J. Bacteriol. 183: 4823-4838). Therefore, instead of or in addition to one or more kinds of the THL-encoding gene, the CTF-encoding gene, and the ADC-encoding gene derived from *Clostridium beijerinckii, Clostridium aurantibutyricum*, and the like that perform butanol-isopropanol fermentation, a THL-encoding gene, a CTF-encoding gene, and an ADC-encoding gene derived from the above-mentioned *Clostridium* bacteria that perform butanol-acetone fermentation may be used, respectively.

Since genomes of more than 600 species have been sequenced so far, it has come to be possible to extract information on a target gene derived from various species and to isolate the gene, based on homology search using gene databases. Therefore, a THL-encoding gene, a CTF-encoding gene, an ADC-encoding gene and an ADH-encoding gene derived from species other than the above-mentioned *Clostridium* bacteria can also be easily isolated. Among such isopropanol production-related genes, those of relatively high homology with the corresponding genes derived from the above-mentioned *Clostridium* bacteria will be exemplified below. Examples of THL-encoding genes include, for example, THL-encoding genes derived from *Clostridium perfringens, Clostridium tetani, Clostridium kluyveri, Clostridium butyricum, Clostridium novyi, Clostridium botulinum, Thermoanaerobacterium thermosaccharolyticum, Thermosinus carboxydivorans, Clostridium difficile, Carboxydothermus hydrogenoformans, Thermoanaerobacter tengcongensis, Desulfotomaculum reducens, Oceanospirillum* sp., *Pseudomonas putida*, etc.

Examples of CTF-encoding genes include those derived from *Thermoanaerobacter tengcongensis, Escherichia coli* K12, etc.

Examples of ADC-encoding genes include those derived from *Saccharopolyspora erythraea, Streptomyces nogalater, Pseudomonas aeruginosa, Streptomyces avermitilis*, etc.

Examples of ADH-encoding genes include those derived from *Rhodococcus ruber, Thermoanaerobacter ethanolicus, Thermoanaerobacter tengcongensis, Thermoanaerobacter brockii, Thermosinus carboxydivorans, Methanosarcina barkeri*, etc.

Therefore, instead of or in addition to one or more kinds of the THL-encoding gene, the CTF-encoding gene, the ADC-encoding gene and the ADH-encoding gene derived from the above-mentioned *Clostridium* bacteria that perform butanol-isopropanol fermentation or butanol-acetone fermentation, a THL-encoding gene, a CTF-encoding gene, an ADC-encoding gene and an ADH-encoding gene derived from, for example, other species mentioned here may be used, respectively as long as the catalytic activity of an enzyme encoded by each gene is the same as that of the corresponding enzyme.

In the present invention, it is preferred to use, as the above (a) to (d) genes, a THL-encoding gene, a CTF-encoding gene, an ADC-encoding gene, and an ADH-encoding gene, derived from a same or different microorganism selected from the group consisting of *Clostridium acetobutylicum, Escherichia coli, Rhodococcus ruber, Clostridium beijerinckii, Clostridium aurantibutyricum, Clostridium saccharoperbutylacetonicum, Clostridium saccharoacetobutylicum, Clostridium pasteurianum, Clostridium sporogenes, Clostridium cadaveris, Clostridium tetanomorphum*, and *Ralstonia eutropha*, respectively.

In the present invention, it is preferred that the above (d) is a gene derived from *Escherichia coli*, and/or the above (d) is gene derived from *Rhodococcus ruber*.

In the present invention, it is most preferred to use, as the above (a) to (d) genes, the THL-encoding gene and the ADC-encoding gene derived from *Clostridium acetobutylicum*, the CTF-encoding gene derived from *Escherichia coli*, and the ADH-encoding gene derived from *Rhodococcus ruber*.

In the present invention, it is preferred that (a) the exogenous gene which encodes an enzyme having acetyl-CoA acetyltransferase activity is a DNA comprising the base sequence of SEQ ID NO: 13, or a DNA which hybridizes to a DNA comprising a complementary base sequence of a DNA comprising the base sequence of SEQ ID NO: 13 under stringent conditions and which encodes a polypeptide having acetyl-CoA acetyltransferase activity;

(b) the exogenous gene which encodes an enzyme having acetoacetyl CoA:acetate CoA-transferase activity is a DNA comprising the base sequence of SEQ ID NO: 14, or a DNA which hybridizes to a DNA comprising a complementary base sequence of a DNA comprising the base sequence of SEQ ID NO: 14 under stringent conditions and which encodes a polypeptide having acetoacetyl CoA:acetate CoA-transferase activity;

(c) the exogenous gene which encodes an enzyme having acetoacetate decarboxylase activity is a DNA comprising the base sequence of SEQ ID NO: 15, or a DNA which hybridizes to a DNA comprising a complementary base sequence of a DNA comprising the base sequence of SEQ ID NO: 15 under stringent conditions and which encodes a polypeptide having acetoacetate decarboxylase activity; and (d) the exogenous gene which encodes an enzyme having isopropanol dehydrogenase activity is a DNA comprising the base sequence of SEQ ID NO: 16, or a DNA which hybridizes to a DNA comprising a complementary base sequence of a DNA comprising the base sequence of SEQ ID NO: 16 under stringent conditions and which encodes a polypeptide having isopropanol dehydrogenase activity.

The DNAs of the base sequences of SEQ ID NOs: 13 and 15 are genes derived from *Clostridium acetobutylicum*. SEQ ID NO: 13 and 15 are the base sequences of the thl gene which encodes THL and the adc gene which encodes ADC, respectively. The DNA of the base sequence of SEQ ID NO: 14 is a gene derived from *Escherichia coli*. Also, SEQ ID NO: 14 is the base sequence of the atoAD gene which encodes CTF. The DNA of the base sequence of SEQ ID NO: 16 is a gene derived from *Rhodococcus ruber*. Also, SEQ ID NO: 16 is the base sequence of the adh gene which encodes ADH.

The "stringent conditions" as used herein means general conditions, for example, the conditions described in Molecular Cloning, A Laboratory Manual, Second edition, Vol. 2, 1989, p. 11.45. It means, in particular, conditions where hybridization occurs at a temperature 5 to 10° C. below the melting temperature (Tm) of a perfect hybrid.

Here, more preferable "stringent conditions" means conditions where hybridization occurs with 90% or more, more preferably 95% or more, and particularly preferably 98% or more sequence homology. Such "stringent conditions" are described in the above Molecular Cloning, A Laboratory Manual, Second edition, Cold Spring Harbor Laboratory Press (1989), particularly in Section 11.45 "Conditions for Hybridization of Oligonucleotide Probes", and the conditions may be used here.

In the present invention, homology values between base sequences were calculated using calculation software GENE-TYX (registered trademark) Ver. 8 (made by Genetics).

Also, in the present invention, a DNA which hybridizes to a DNA under stringent conditions, for example, a DNA which hybridizes to a DNA comprising a complementary base sequence of a DNA comprising the base sequence of SEQ ID NO: 13 under stringent conditions, preferably has about 90% or more, more preferably about 95% or more, and particularly preferably about 98% or more sequence homology with the base sequence of SEQ ID NO: 13.

In the polymerase chain reaction (PCR) method, the oligonucleotide primer sets shown below may be used to amplify each sequence of a THL-encoding exogenous gene, a CTF-encoding exogenous gene, an ADC-encoding exogenous gene and an ADH-encoding exogenous gene derived from various kinds of living organisms. Examples of such primer sets include the primer set represented by base sequences of SEQ ID NOs: 1 and 2 for amplifying a THL-encoding gene, the primer set represented by base sequences of SEQ ID NOs: 5 and 6 for amplifying a CTF-encoding gene, the primer set represented by base sequences of SEQ ID NOs: 3 and 4 for amplifying an ADC-encoding gene, the primer set represented by base sequences of SEQ ID NOs: 7 and 8 for amplifying an ADH-encoding gene, etc.

In the PCR method, a known PCR device, for example a thermal cycler, may be used. The PCR cycle may be performed according to known techniques. For example, a cycle of denaturation, annealing and extension is repeated usually 10 to 100 times, preferably about 20 to 50 times. Templates used in the PCR to amplify cDNA of a THL-encoding gene, a CTF-encoding gene, an ADC-encoding gene, and an ADH-encoding gene may be DNAs isolated from a microorganism which exhibits the enzyme activity responsible for the above-mentioned isopropanol-producing pathway. A gene obtained by the PCR method may be transferred into a suitable cloning vector. As the cloning method, commercially available PCR cloning systems, such as pGEM-T easy vector system (made by Promega), TOPO TA-cloning system (made by Invitrogen), Mighty Cloning Kit (made by Takara), etc. may be used. Alternatively, a DNA fragment comprising the corresponding region may be obtained by a hybridization method using, as a template, synthetic primers suitably designed based on a known THL-encoding gene, a known CTF-encoding gene, a known ADC-encoding gene, or a known ADH-encoding gene. An example of such a method will be described in detail in Examples.

Construction of Vector

Subsequently, a cloning vector comprising a gene obtained by the PCR method is transferred into a microorganism, for example, *Escherichia coli* JM109 strain for transformation. The transformed strain is cultured in a culture medium containing suitable antibiotics (for example, ampicillin, chloramphenicol, etc.), and cells are collected from the culture. From the collected cells, plasmid DNA is extracted. The extraction of the plasmid DNA can be performed using a known technique. A commercial plasmid extraction kit may also be used for easy extraction. Examples of the commercial plasmid extraction kit include Qiaquick plasmid purification kit (trade name) made by QIAGEN. By determining the base sequence of this extracted plasmid DNA, the existence of the sequences of a THL-encoding gene, a CTF-encoding gene, an ADC-encoding gene, and an ADH-encoding gene can be confirmed. The base sequence of the DNA can be determined by a known method, for example, the dideoxychain termination method etc. Alternatively, the base sequence can also be determined using a capillary electrophoretic system which utilizes multi-fluorescence technique for detection. Alternatively, the base sequence can also be determined using a DNA sequencer, for example, ABI PRISM 3730×1 DNA Analyzer (made by Applied Biosystem) etc.

The above-mentioned methods can be performed based on conventional methods of genetic engineering experiments. Vectors of various kinds of microorganisms, and methods for transfer and expression of exogenous genes are described in many experimental books (for example, Sambrook, J. & Russell, D. W. Molecular Cloning: A Laboratory Manual (3rd Edition) CSHL Press (2001), or Ausubel, F. et al. Current protocols in molecular biology. Green Publishing and Wiley InterScience, New York (1987), etc). Therefore, selection of vectors, and transfer and expression of genes can be performed according to these books.

A wide variety of promoters can suitably be used in the present invention. Such a promoter may be obtained from many known supply sources including yeast, bacteria, and other cell supply sources and may be any base sequence as long as it has a function to start transcription of a target gene in a coryneform bacterium. As suitable examples of such a promoter, the lac promoter, the trc promoter, the tac promoter, etc. can be used in a coryneform bacterium. The promoter used in the present invention may be modified for change in its regulatory mechanism. The terminator placed downstream of a target gene under a regulatory sequence may also be any base sequence as long as it has a function to terminate transcription of the gene in a coryneform bacterium.

Next, a THL-encoding gene, a CTF-encoding gene, an ADC-encoding gene, and an ADH-encoding gene are expressed on a plasmid or a chromosome in the coryneform bacterium mentioned above. For example, using a plasmid, these genes are transferred under a regulatory sequence so as to be expressible. Herein, "under a regulatory sequence" means that cooperative work of these genes with, for example, a promoter, an inducer, an operator, a ribosome binding site and a transcription terminator can achieve transcription and translation. A plasmid vector used for such a purpose may be any plasmid vector as long as it comprises a gene responsible for autonomous replicating in a coryneform bacterium. Specific examples of the plasmid vector include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)); pHM1519 derived from *Corynebacterium glutamicum* ATCC13058 (Miwa, K. et al., Cryptic plasmids in glutamic acid-producing bacteria. Agric., Biol., Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from *Corynebacterium glutamicum* T250 (JP 57-183799 A; and Katsumata, R. et al., Protoplast transformation of glutamate-producing bacteria with plasmid DNA. J. Bacteriol., 159:306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum/Escherichia coli* shuttle vectors for cloning, controlled gene expression, and promoter probing. Gene, 102:93-98 (1991)); derivatives thereof; etc. Phage DNA etc. are also included, and any other vector can be used as long as it can reproduce in a host. The vector preferably includes a multi-cloning site which has various kinds of restriction enzyme sites inside, or a single restriction enzyme site.

The plasmid vector used for creating a transformed coryneform bacterium of the present invention, for example in the case where the THL-encoding gene and the ADC-encoding gene derived from *Clostridium acetobutylicum*, the CTF-encoding gene derived from *Escherichia coli*, and the ADH-encoding gene derived from *Rhodococcus ruber* are used, can be constructed by ligating each of the genes whose base sequences have already been confirmed to a suitable regulatory sequence such as promoters and terminators, and subsequently inserting in a suitable restriction enzyme site of one of the above-mentioned plasmid vectors. Details are described in Examples.

Transformation

The method for transferring a plasmid vector comprising a target gene into *Escherichia coli* and a coryneform bacterium may be a known method, such as electroporation, the calcium chloride/rubidium chloride method, the calcium phosphate method, and the DEAE-dextran transfection. Specifically, in the case of *Escherichia coli* for example, the calcium chloride method or the electroporation (for example, Sambrook, J. & Russell, D. W. Molecular Cloning: A Laboratory Manual (3rd Edition) CSHL Press (2001); or Ausubel, F. et al. Current protocols in molecular biology. Green Publishing and Wiley InterScience, New York (1987) etc.), may be used. Also, a method with use of *Escherichia coli* JM109 Competent Cells (made by TAKARA SHUZO) may be performed according to the company's protocol. In the case of coryneform bacteria, an electric pulse method may be performed by a known method (Kurusu, Y. et al., Electroporation-transformation system for Coryneform bacteria by auxotrophic complementation., Agric., Biol. Chem. 54:443-447 (1990); and Vertes A.

A. et al., Presence of mrr- and mcr-like restriction systems in Coryneform bacteria. Res. Microbiol. 144:181-185 (1993)).

The above methods may be performed based on a conventional method for gene engineering experiments. Information on vectors of various kinds of microorganisms, such as *Escherichia coli* and Actinomycetes, and methods for transfer and expression of exogenous genes are described in many experimental books (for example, Sambrook, J. & Russell, D. W. Molecular Cloning: A Laboratory Manual, 3rd Edition, CSHL Press, 2001; Hopwood, D. A., Bibb, M. J., Charter, K. F., Bruton, C. J., Kieser, H. M., Lydiate, D. J., Smith, C. P., Ward, J. M., Schrempf, H. Genetic manipulation of *Streptomyces*: A Laboratory manual, The John Innes institute, Norwich, UK, 1985; etc.). Therefore, selection of vectors, and transfer and expression of genes can be performed according to these books.

Specific examples of the transformant of a coryneform bacterium created by a method described above include *Corynebacterium glutamicum* ISO1 (deposited under Accession Number NITE BP-561) and *Corynebacterium glutamicum* ISO2 (deposited under Accession Number NITE BP-562), both deposited in Incorporated Administrative Agency National Institute of Technology and Evaluation, NITE Patent Microorganisms Depositary (2-5-8 Kazusakamatari, Kisarazu-shi, Chiba 292-0818 Japan) on Apr. 15, 2008). These transformants are also included in the present invention.

For improving production of isopropanol, the transformant of the present invention may include genetic modification which leads to one or more characteristics selected from the group consisting of increased flow in glycolytic system, increased resistance to isopropanol, osmotic pressure or organic acids, and reduced production of by-products (carbon-containing molecules other than the target product). Such genetic modification can be introduced, in particular, by overexpression of an exogenous gene and/or inactivation of an endogenous gene, classic mutagenesis, screening and/or target mutant selection.

A transformant may be mutated by artificial mutagenesis with the use of ultraviolet, X-rays, or an agent. Any mutant obtained in such a way may be used as a transformed microorganism of the present invention, as long as it is capable of producing isopropanol, achieving the object of the present invention.

The thus created transformant of a coryneform bacterium of the present invention (hereinafter referred to simply as the transformant) may be cultured using a culture medium commonly used for culture of microorganisms. The culture medium may be a natural medium or a synthetic medium containing a carbon source, a nitrogen source, inorganic salts, other nutritional substances, etc.

Examples of the carbon source include, for example, carbohydrates and sugar alcohols such as glucose, fructose, sucrose, mannose, maltose, mannitol, xylose, galactose, starch, molasses, sorbitol and glycerol; organic acids such as acetic acid, citric acid, lactic acid, fumaric acid, maleic acid and gluconic acid; and alcohols such as ethanol. Hydrocarbons, such as normal paraffin, etc. may be used if desired. These carbon sources may be used alone or as a mixture of two or more thereof. The concentration of these carbon sources in a culture medium is usually about 0.1 to 10% by weight and preferably about 0.5 to 10% by weight.

Examples of the nitrogen source include nitrogen compounds inorganic or organic ammonium compounds such as ammonium chloride, ammonium sulfate, ammonium nitrate, and ammonium acetate; urea; aqueous ammonia; sodium nitrate; and potassium nitrate, but the nitrogen source is not limited thereto. Nitrogen-containing organic compounds, such as corn steep liquor, meat extract, peptone, N—Z-amine, protein hydrolysate, amino acid, etc. may be used. These nitrogen sources may be used alone or as a mixture of two or more thereof. The concentration of these nitrogen sources in a culture medium varies depending on the kind of the nitrogen compound, but is usually about 0.1 to 10% by weight and preferably about 0.5 to 10% by weight.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of these inorganic salts in a culture medium varies depending on the kind of the inorganic salt, but is usually about 0.01 to 1% by weight and preferably about 0.05 to 1% by weight.

Examples of the nutritional substances include meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of these nutritional substances in a culture medium varies depending on the kind of the nutritional substance, but is usually about 0.1 to 10% by weight and preferably about 0.5 to 10% by weight. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)) etc.

The culture temperature is usually about 15 to 45° C., preferably about 25 to 35° C., and the culture period is about 1 to 7 days.

Subsequently, cultured bacterial cells of the transformant are collected. The method for collecting and isolating cultured bacterial cells from the culture obtained as described above is not particularly limited, and any known method, such as centrifugal separation and membrane separation, may be used.

The collected bacterial cells may be subjected to some treatment and then the resulting treated bacterial cells may be used in the next step. As long as the cultured bacterial cells have undergone some treatment, they can be used as the treated bacterial cells. Examples of the treated bacterial cells include immobilized bacterial cells obtained by treatment with, for example, acrylamide, carrageenan, or the like.

(II) Method for Producing Isopropanol

The cultured bacterial cells of the transformant collected and isolated from the culture or treated bacterial cells thereof obtained as described above are subjected to isopropanol-producing reaction in a reaction culture medium usually under aerobic or anaerobic conditions. The method for producing isopropanol comprising a step of culturing the above-mentioned transformant in a culture medium containing saccharides (reaction culture medium) and a step of collecting isopropanol from the culture is also comprised in the present invention.

The method for producing isopropanol may be any of a batch method, a fed-batch method, and a continuous method.

The reaction culture medium (reaction mixture) may be any culture medium as long as it contains an organic carbon source (for example, saccharides etc.) as a raw material of isopropanol. The organic carbon source may be any substance as long as the transformant of the present invention can utilize the substance for a biochemical reaction.

Specific examples of saccharides include monosaccharides such as glucose, xylose, arabinose, galactose, fructose and mannose; disaccharides such as cellobiose, sucrose, lactose and maltose; poly saccharides such as dextrin and soluble starch; etc. In particular, monosaccharides such as $C_6$ sugars and $C_5$ sugars are preferred. However, in some cases, coryneform bacteria cannot assimilate $C_5$ monosaccharides such as xylose, arabinose, etc. In such cases, a function to assimilate those monosaccharides should be given to the bacteria. In the present invention, a mixture of two or more kinds of saccharides may also be used.

More preferably, the reaction culture medium used for a reaction for producing an organic compound usually contains ingredients necessary for the transformant or treated transformant to maintain its metabolic functions, that is, carbon sources such as various saccharides; nitrogen sources necessary for protein synthesis; and others including salts of phosphorus, potassium, sodium, etc. and salts of trace metals such as iron, manganese and calcium. The amounts of such ingredients may be suitably determined depending on the necessary reaction time, the target organic compound, or the transformant to be used. Depending on the transformant to be used, addition of certain vitamins may be preferred. The carbon source, the nitrogen source, the inorganic salts, the vitamin, and the trace metal salt to be used may be known ingredients, for example, those illustrated in the step of proliferation and culturing.

Usually, preferred pH of the reaction culture medium is about 6 to 8.

The reaction of the transformant or treated bacterial cells thereof with saccharides is preferably performed under temperature conditions in which the transformant of the present invention or treated bacterial cells thereof can work. The temperature may be suitably determined depending on the transformant or treated bacterial cells thereof, etc., and is usually about 25 to 35° C.

Finally, isopropanol produced in a reaction culture medium as described above is collected. A known method used in the field of bioprocess may be used. Examples of such a known method for collecting produced isopropanol include distillation, membrane permeation method, organic solvent extraction method, etc. The method for separation, purification and collection may be suitably determined depending on the composition of the reaction mixture, by-products, etc.

The present invention further provides a recombinant isopropanol-producing transformant with remarkably improved capability to produce isopropanol from saccharides etc. by a reaction under the conditions described above.

EXAMPLES

Hereinafter, the present invention will be illustrated in more detail by Examples, but is not limited thereto.

Example 1

Creation of *Corynebacterium glutamicum* ISO1 and *Corynebacterium glutamicum* ISO2

(1) Cloning of a Group of Isopropanol-Producing Genes

The isopropanol biosynthesis pathway (from acetyl CoA to isopropanol) consists of 4 steps involving 4 enzymes i.e., acetyl-CoA acetyltransferase, acetoacetyl CoA:acetate CoA-transferase, acetoacetate decarboxylase, and isopropanol dehydrogenase. Respective genes which encode these 4 enzymes were amplified by the PCR method as described below.

Using chromosomal and plasmid DNAs of *Clostridium acetobutylicum* ATCC 824 (ATCC 824D-5) obtained from American Type Culture Collection (ATCC) as templates, and using primers 1 and 2 (SEQ ID NOs: 1 and 2), and primers 3 and 4 (SEQ ID NOs: 3 and 4), an acetyl-CoA acetyltransferase gene (thl), and an acetoacetate decarboxylase gene (adc) were respectively amplified by PCR. Using chromosomal DNA of *Escherichia coli* JM109 as template, and using primers 5 and 6 (SEQ ID NOs: 5 and 6), an acetoacetyl CoA:acetate CoA-transferase gene (atoAD) was amplified by PCR. PCR was performed using GeneAmp PCR System 9700 (made by Applied Biosystems) under the conditions of PCR Reaction 1 (30 cycles of 94° C. for 30 seconds, 58° C. for 30 seconds, and 72° C. for 1.5 minutes; template DNA 10 ng; reaction mixture: dNTP 0.2 mM, PrimeSTAR DNA polymerase (made by TAKARA) 2 U, 5×PrimeSTAR buffer 6 µL, and each primer 0.2 µM; final volume 30 µL). Using 3 µL of the above amplified reaction mixture, 0.8% agarose gel electrophoresis was performed. In the case of the thl gene, the atoAD gene, and the adc gene, about 1.2-kb, about 1.3-kb, and about 0.7-kb DNA fragments were respectively detected. The amplified DNA fragments were purified using MinElute PCR Purification Kit (made by QIAGEN).

*Rhodococcus ruber* DSM 44541 was liquid-cultured with shaking in Trypticase peptone medium (made by Becton Dickinson) at 30° C. After 16-hour culture, 5 mL of the culture medium was centrifuged (high speed refrigerated micro centrifuge MX-301 made by TOMY SEIKO, 5,000 rpm, 10 minutes), and precipitated bacterial cells were subjected to extraction of chromosomal DNA. The extraction of chromosomal DNA was performed using Isoplant II (made by NIPPON GENE) according to the attached protocol. Using the chromosomal DNA of *Rhodococcus ruber* DSM 44541 as a template, and using primers 7 and 8 (SEQ ID NOs: 7 and 8), an isopropanol dehydrogenase gene (adh) was amplified under the conditions of the above-mentioned PCR Reaction 1. Using 3 µL of the above amplified reaction mixture, 0.8% agarose gel electrophoresis was performed, and an about 1.0-kb DNA fragment comprising the adh gene was detected. The amplified DNA fragment was purified using MinElute PCR Purification Kit.

In order to obtain a gene expression promoter (tac promoter), using pKK223-3 (made by Pharmacia) as a template, and using primers 9 and 10 (SEQ ID NOs: 9 and 10), an about 0.2-kb DNA fragment comprising a tac promoter was amplified under the conditions of the above-mentioned PCR Reaction 1. After the end of the reaction, the amplified DNA fragment was purified using MinElute PCR Purification Kit (made by QIAGEN).

Ligation of the tac promoter with the about 1.3-kb DNA fragment comprising the atoAD gene, the about 0.7-kb DNA fragment comprising the adc gene, or the about 1.0-kb DNA fragment comprising the adh gene, obtained in the above-mentioned PCR Reaction 1, was performed in the following procedure. That is, each of the above three kinds of DNA fragments, and the DNA fragment comprising the tac promoter were mixed in amounts of about 100 ng each. To this, 0.2 mM of dNTP, 2 U of PrimeSTAR DNA polymerase (made by TAKARA), and 6 µL of 5×PrimeSTAR buffer were added and mixed so that the final volume might be 30 µL. This reaction mixture was reacted using GeneAmp PCR System 9700 under the conditions of PCR Reaction 2 (30 cycles of 94° C. for 30 seconds, 52° C. for 30 seconds, and 72° C. for 1.5 minutes). After the end of the reaction, in order to obtain a DNA fragment in which the tac promoter was ligated to the atoAD, adc or adh gene, 0.5 µL of the reaction mixture as a template was amplified by PCR under the conditions of the above-mentioned PCR Reaction 1 using primers 6 and 9, primers 4 and 11 (SEQ ID NO: 11), or primers 8 and 12 (SEQ ID NO: 12). Using 3 µL of the above amplified reaction mixture, 0.8% agarose gel electrophoresis was performed. As a result, an about 1.5-kb DNA fragment comprising the atoAD gene ligated to the tac promoter (Ptac-atoAD), an about 0.9-kb DNA fragment comprising the adc gene ligated to the tac promoter (Ptac-adc), and an about 1.2-kb DNA fragment comprising the adh gene ligated to the tac promoter (Ptac-adh) were detected. Each DNA fragment was separated by agarose gel electrophoresis and then collected from the gel using MinElute Gel Extraction Kit (made by QIAGEN).

The above-mentioned about 1.2-kb thl DNA fragment without any ligated tac promoter, about 1.5-kb DNA fragment comprising the Ptac-atoAD, about 0.9-kb DNA fragment comprising the Ptac-adc, or about 1.2-kb DNA fragment comprising the Ptac-adh was ligated to a pGEM-T vector (made by Promega) according to the instruction manual, and *Escherichia coli* JM109 was transformed by the calcium chloride method (Journal of Molecular Biology, 53, and 159 (1970)). The resultant solution was applied to LB agar medium (10 g of poly peptone, 5 g of yeast extract, 5 g of NaCl, and 15 g of agar were dissolved in 1 L of distilled water) containing 50 µg/mL of ampicillin. In each case, growing strains on the culture medium were subjected to liquid culture in the usual manner. Plasmid DNA was extracted from the culture medium and cut with the use of restriction enzymes to confirm the inserted fragment. Furthermore, sequencing of the inserted fragment was performed to confirm that the target DNA sequence had been constructed. A plasmid comprising the thl gene (SEQ ID NO: 13), a plasmid comprising the atoAD gene (SEQ ID NO: 14), a plasmid comprising the adc gene (SEQ ID NO: 15) and a plasmid comprising the adh gene (SEQ ID NO: 16) were named pGEM-thl, pGEM-Ptac-atoAD, pGEM-Ptac-adc, and pGEM-Ptac-adh, respectively. ABI PRISM3100 (made by Applied Biosystems) as a DNA sequencer, and ABI PRISM Cycle Sequencing Kit (made by Applied Biosystems) for sequence reaction were used. The plasmids pGEM-thl, pGEM-Ptac-atoAD, pGEM-Ptac-adc and pGEM-Ptac-adh thus prepared were cut with the use of restriction enzymes EcoRI and BamHI, BamHI and SphI, SphI and SmaI, and EcoRI, respectively, and then each of them was separated by agarose gel electrophoresis. Using MinElute Gel Extraction Kit (made by QIAGEN) for collection from the gel, an about 1.2-kb EcoRI-BamHI DNA fragment comprising the thl gene without any ligated tac promoter, an about 1.5-kb BamHI-SphI DNA fragment comprising the Ptac-atoAD gene comprising the tac promoter, an about 0.9-kb SphI-SmaI DNA fragment comprising the Ptac-adc gene comprising the tac promoter, and an about 1.2-kb EcoRI DNA fragment comprising the Ptac-adh gene comprising the tac promoter were obtained.

(2) Construction of Expression Plasmids pCRA725-SSI11-ACE and pCRC203, and Creation of *Corynebacterium glutamicum* ISO1 and *Corynebacterium glutamicum* ISO2

The DNA fragments obtained in the above (1), that is, the about 1.2-kb EcoRI-BamHI DNA fragment comprising the thl gene without any ligated tac promoter, the about 1.5-kb BamHI-SphI DNA fragment comprising the Ptac-atoAD gene comprising the tac promoter, and the about 0.9-kb SphI-SmaI DNA fragment comprising the Ptac-adc gene comprising the tac promoter, in amounts of 100 ng each, and 10 ng of pCRC200 (Applied Microbiology and Biotechnology. 77:853-860, 2007) digested by EcoRI and SmaI beforehand were all mixed, and ligation was performed using DNA ligation kit. Since pCRC200 comprises a tac promoter upstream of the cloning site, the thl gene will also have the tac promoter ligated thereto as a result. *Escherichia coli* JM109 was transformed by the calcium chloride method using this ligation liquid, and by selecting, on the basis of chloramphenicol resistance, an *Escherichia coli* strain carrying a plasmid DNA comprising the target gene fragments, plasmid pCRC203 was obtained (FIG. 1, SEQ ID NO: 17).

Subsequently, for markerless introduction of the thl-atoAD-adc gene set having a ligated tac promoter into a chromosome of *Corynebacterium glutamicum* R, a chromosome region which is not indispensable for the microorganism to grow was determined based on Appl. Environ. Microbiol., Vol. 71, 3369-3372, 2005, and it was decided to insert the thl-atoAD-adc gene set into the chromosome region SSI11. The DNA sequence of this SSI11 region was amplified by the PCR method as described below.

In the PCR, primers 13 and 14 (SEQ ID NOs: 18 and 19) were used. Each primer has one XbaI site added to the end thereof.

As the template DNA, the chromosomal DNA of *Corynebacterium glutamicum* R was used. The extraction of chromosomal DNA was performed using Isoplant II (made by NIPPON GENE) according to the attached protocol. The PCR was performed under the conditions of PCR Reaction 3 (30 cycles of 94° C. for 30 seconds, 55° C. for 30 seconds, and 72° C. for 3 minutes) with the use of the LA Taq HS DNA polymerase (made by TAKARA). The composition of the PCR reaction mixture is shown below.

Reaction Mixture Composition

| | |
|---|---|
| (10×) PCR buffer soln.: | 10 µL |
| 2.5 mM dNTP Mix: | 8 µL |
| Template DNA: | 2 µL (DNA content: 500 ng or less) |
| The above 2 primers: | 0.5 µL each (final conc.: 0.2 µM) |
| LA Taq HS DNA polymerase: | 0.5 µL |
| Sterile distilled water: | 79 µL |

The above ingredients were mixed and the PCR reaction was performed.

Using the above prepared reaction mixture, 0.8% agarose gel electrophoresis was performed, and an about 2.0-kb DNA fragment comprising the SSI11 region was detected.

The amplification product treated with the above-mentioned restriction enzyme XbaI and the plasmid for chromosomal gene transfer, pCRA725 treated with XbaI (J. Mol. Microbial. Biotechnol., Vol. 8, 243-254, 2004) (JP 2006-124440 A) were mixed. After addition of Mighty Cloning Kit (made by TAKARA) thereto, the mixture was made to react according to the instruction manual. *Escherichia coli* JM109 was transformed by the calcium chloride method using this ligation liquid, and by selecting an *Escherichia coli* strain carrying a plasmid DNA comprising the target gene fragments, plasmid pCRA725-SSI11 having an inserted about 2.0-kb DNA fragment comprising an SSI11 region was obtained (FIG. 1, SEQ ID NO: 20).

Using the plasmid pCRC203 as a template, and using 5'-phosphorylated primers 15 and 16 (SEQ ID NOs: 21 and 22), the thl-atoAD-adc gene set was amplified by the PCR method. Using 3 µL of the above amplified reaction mixture, 0.8% agarose gel electrophoresis was performed, and an about 3.8-kb DNA fragment having the thl gene, the atoAD gene, and the adc gene each ligated to the tac promoter was detected. The DNA fragment was separated by agarose gel electrophoresis and then collected from the gel using MinElute Gel Extraction Kit (made by QIAGEN). After 10 ng of pCRA725-SSI11 which was pretreated with EcoRV and subsequently dephosphorilated with alkaline phosphatase (made by TAKARA) and 100 ng of the DNA fragment were mixed, ligation was performed using DNA ligation kit. *Escherichia coli* JM109 was transformed by the calcium chloride method using this ligation liquid, and by selecting an *Escherichia coli* strain carrying a plasmid DNA comprising the target gene fragments, plasmid pCRA725-SSI11-ACE was obtained (FIG. 1, SEQ ID NO: 23).

Vector pCRA725 for chromosomal gene transfer is a plasmid that cannot be replicated within *Corynebacterium glutamicum* R. By an electric pulse method (Agric. Biol. Chem., Vol. 54, 443-447, 1990; and Res. Microbiol., Vol. 144, 181-185, 1993), *Corynebacterium glutamicum* R and *Corynebacterium glutamicum* R ldhA mutant (J. Mol. Microbiol. Biotechnol., Vol. 8, 243-254, 2004) were separately transformed with the use of the plasmid pCRA725-SSI11-ACE, and the transfected strains were selected with the use of A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar (per liter)) containing 50 µg/mL of kanamycin.

The obtained recombinant strains were named *Corynebacterium glutamicum* ACE1 and *Corynebacterium glutamicum* ACE2, respectively.

Figure 2:
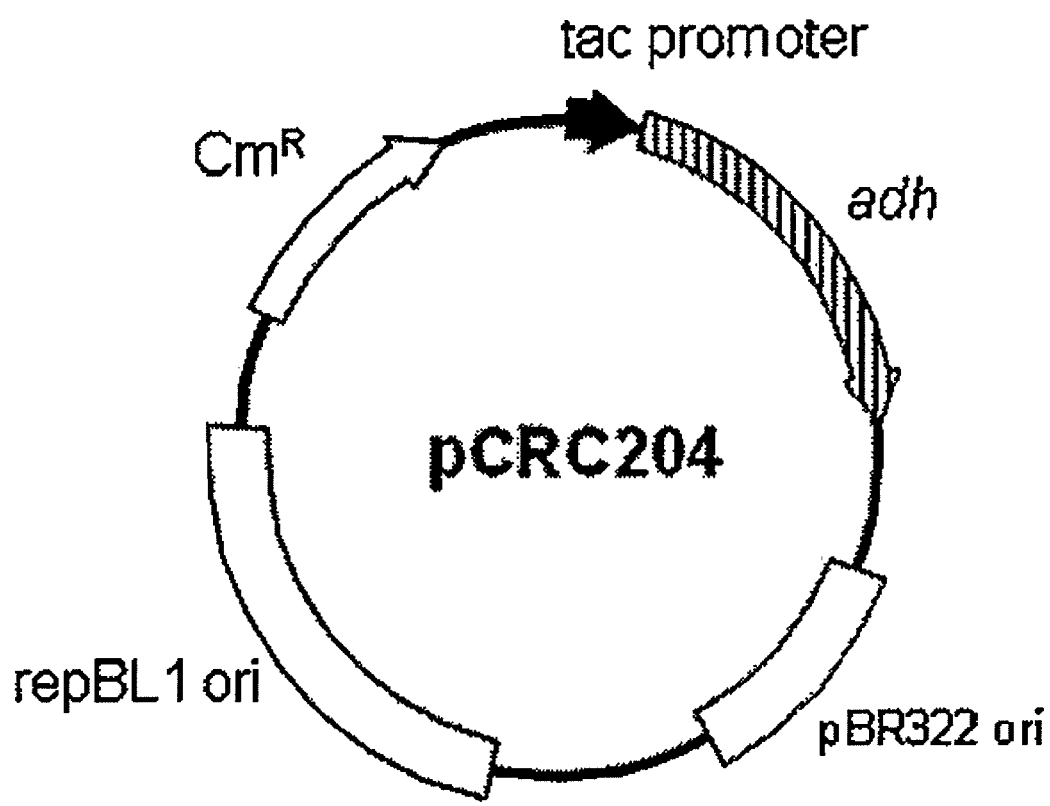
FIG. 2 is a schematic view showing the plasmid pCRC204 prepared in Example 1 (2).

A plasmid was prepared by inserting the about 1.2-kb DNA fragment comprising an adh gene having a ligated tac promoter obtained in the above (1) into the EcoRI site of pCRB1, which is a self-replicable plasmid of *Corynebacterium glutamicum* (American Chemical Society Symposium Series 862: Fermentation Biotechnology, American Chemical Society, Washington, 175-191, 2003). Specifically, after 10 ng of pCRB1 which was pretreated with EcoRI and subsequently dephosphorilated with alkaline phosphatase and 100 ng of the EcoRI DNA fragment comprising an adh gene having a ligated tac promoter were mixed, ligation was performed using DNA ligation kit. *Escherichia coli* JM109 was transformed by the calcium chloride method using this ligation liquid, and by selecting an *Escherichia coli* strain carrying a plasmid DNA comprising the target gene fragments, plasmid pCRC204 was obtained (FIG. 2, SEQ ID NO: 24). By an electric pulse method, *Corynebacterium glutamicum* ACE1 and *Corynebacterium glutamicum* ACE2 were transformed with the use of the plasmid pCRC204. The transformed strains were selected with the use of A agar medium containing 50 µg/mL of kanamycin and 5 µg/mL of chloramphenicol. The obtained recombinant strains were named *Corynebacterium glutamicum* ISO1 and *Corynebacterium glutamicum*

ISO2, respectively. These recombinant strains were deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Numbers NITE BP-561 and NITE BP-562 on Apr. 15, 2008.

Example 2

Experiment of Isopropanol Production using *Corynebacterium glutamicum* ISO1 and *Corynebacterium glutamicum* ISO2 Under Aerobic Conditions The *Corynebacterium glutamicum* ISO1 and *Corynebacterium glutamicum* ISO2 created in the above Example 1 (2) were separately applied to A agar medium containing 5 µg/mL of chloramphenicol and 50 µg/mL of kanamycin, and left stand in the dark at 30° C. for 20 hours.

An inoculation loop of the *Corynebacterium glutamicum* ISO1 and *Corynebacterium glutamicum* ISO2 each grown on a plate as above were separately inoculated in a test tube containing 10 mL of A liquid medium (prepared by removing agar from A agar medium) containing 5 µg/mL of chloramphenicol and 50 µg/mL of kanamycin, and aerobically cultured with shaking at 30° C. for 15 hours.

The *Corynebacterium glutamicum* ISO1 and *Corynebacterium glutamicum* ISO2 each grown in the above conditions were separately inoculated in a 500-mL conical flask containing 100 mL of A liquid medium containing 5 µg/mL of chloramphenicol and 50 µg/mL of kanamycin, and aerobically cultured with shaking at 30° C. Every 12 hours, 2.5 g of sodium hydrogen carbonate was added to the culture medium.

For quantitative determination of isopropanol, the reaction mixture sampled was centrifuged (15,000×g at 4° C. for 10 minutes), and obtained supernatant was analyzed by GC/MS. The GC/MS analysis was performed with the use of a gas chromatography/mass spectrometer (GC-MS QP-2010-plus made by Shimadzu) equipped with a DB-WAX capillary column (30 m×0.25 mm×0.25 µm; made by J&W Scientific, USA). The analysis was performed under the following conditions: The flow rate of helium gas and the split ratio were set to 1.0 mL/min and 1:20, respectively, and the GC oven was kept at 40° C. for 5 minutes and then raised up to 230° C. at a heating rate of 10° C./min. The analytical time for each sample was 24 minutes. Conditions of mass spectrometry were as follows: interface, 250° C.; ion source, 200° C.; and electron impact voltage, 70 eV.

In 34 hours, *Corynebacterium glutamicum* ISO1 produced 55 µM of isopropanol, and *Corynebacterium glutamicum* ISO2 produced 1300 µM of isopropanol.

Example 3

Experiment of Isopropanol Production using *Corynebacterium glutamicum* ISO1 and *Corynebacterium glutamicum* ISO2 Under Reducing (Proliferation Inhibiting) Conditions The *Corynebacterium glutamicum* ISO1 and *Corynebacterium glutamicum* ISO2 created in the above Example 1 (2) were separately applied to A agar medium containing 5 µg/mL of chloramphenicol and 50 µg/mL of kanamycin, and left stand in the dark at 30° C. for 20 hours.

An inoculation loop of the *Corynebacterium glutamicum* 1501 and *Corynebacterium glutamicum* 1502 each grown on a plate as above were separately inoculated in 10 mL of A liquid medium in a test tube (prepared by removing agar from A agar medium) containing 5 µg/mL of chloramphenicol and 50 µg/mL of kanamycin, and aerobically cultured with shaking at 30° C. for 15 hours.

The *Corynebacterium glutamicum* 1501 and *Corynebacterium glutamicum* 1502 each grown in the above conditions were separately inoculated in a 2-L conical flask containing 500 mL of A liquid medium containing 5 µg/mL of chloramphenicol and 50 µg/mL of kanamycin, and aerobically cultured with shaking at 30° C. for 15 hours.

Each kind of the bacterial cells cultured and proliferated as above was collected by centrifugation (5,000×g at 4° C. for 15 minutes). Each kind of the obtained bacterial cells were separately suspended in BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the final concentration of the bacterial cell was 5%. To 100-mL medium bottles containing 50 mL of either of the cell suspensions, were added glucose and $NaHCO_3$ so that the concentrations of glucose and $NaHCO_3$ were 200 mM and 150 mM, respectively, and the reaction proceeded in a water bath kept at 33° C. with stirring. Glucose and $NaHCO_3$ were added at 8 hours and 34 hours after the reaction started so that the concentrations of glucose and $NaHCO_3$ were 200 mM and 150 mM, respectively. During the reaction, 5N aqueous ammonia was added with the use of a pH controller (Type: DT-1023 made by Able) to avoid the pH of the reaction mixture falling below 7.5. The quantitative determination of isopropanol was performed by the method described in the above Example 2. During the reaction, each bacterial cell concentration did not change. This fact indicates that proliferation of the bacterial cells was inhibited.

In 34 hours, *Corynebacterium glutamicum* ISO1 produced 790 µl of isopropanol and *Corynebacterium glutamicum* ISO2 produced 332 µM of isopropanol in the respective reaction mixtures.

Example 4

Proliferation of *Escherichia coli* JM109/pCRC202 and *Corynebacterium glutamicum* ISO2 in the Presence of Isopropanol An isopropanol producing strain, *Escherichia coli* JM109/pCRC202 (JP 2007-222633 A; Accession Number FERM P-21340), was inoculated in 3 mL of LB (Luria-Bertani) medium (1% trypton, 0.5% yeast extract and 0.5% sodium chloride) containing 50 µg/mL of chloramphenicol, and *Corynebacterium glutamicum* ISO2 prepared in Example 1 was inoculated in A liquid medium (2 g of $(NH_2)_2CO_3$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose were dissolved in 1 L of distilled water) containing 5 µg/mL of chloramphenicol and 50 µg/mL of kanamycin. The *Escherichia coli* JM109/pCRC202 and the *Corynebacterium glutamicum* were cultured with shaking at 37° C. and 33° C., respectively for 16 hours.

The *Escherichia coli* JM109/pCRC202 and *Corynebacterium glutamicum* ISO2 each grown in the above conditions were inoculated in 10 mL of LB medium (containing 50 µg/mL of chloramphenicol) and 10 mL of A liquid medium (containing 5 μg/mL of chloramphenicol and 50 μg/mL of kanamycin), respectively, each medium in a test tube containing a varied concentration of isopropanol (0 to 5.0% (vol/vol)). The *Escherichia coli* JM109/pCRC202 and the *Corynebacterium glutamicum* were aerobically cultured with shaking at 37° C. and 33° C., respectively for 16 hours, and turbidity measurement was performed over time. For measurement of turbidity, Novaspec II spectrophotometer (Amersham Pharmacia biotech) was used.

Figure 3:
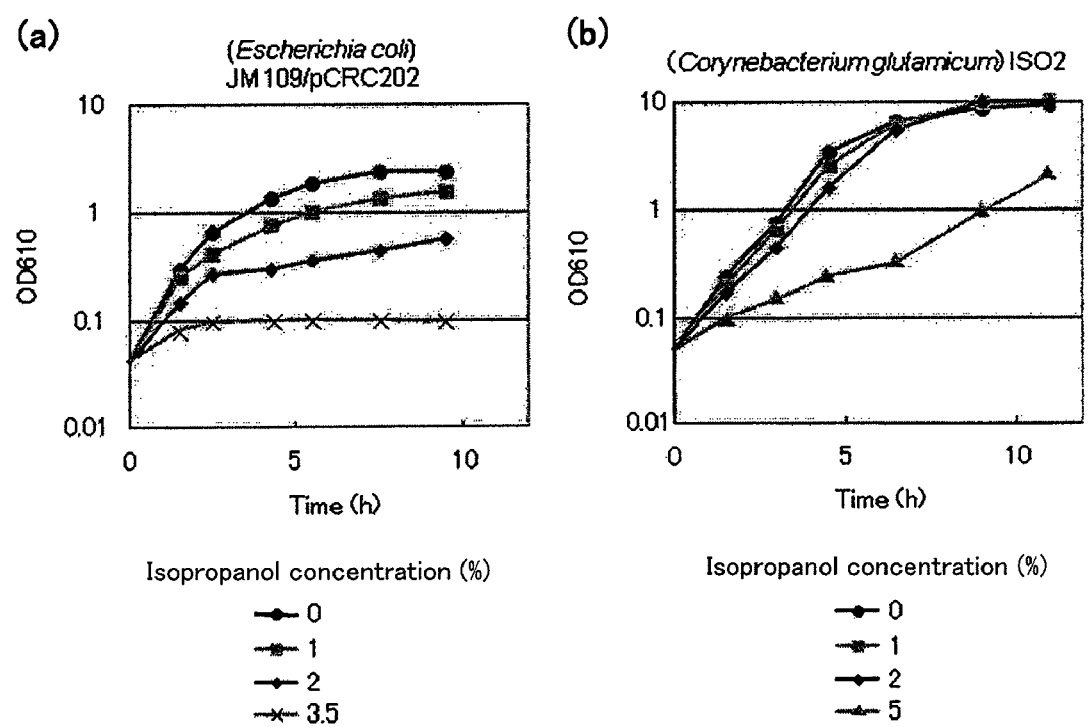
FIG. 3 shows proliferation curves of *Escherichia coli* JM109/pCRC202 and *Corynebacterium glutamicum* ISO2 in the presence of isopropanol.

The results show that while *Escherichia coli* JM109/pCRC202 did not proliferate in the presence of 3.5% isopropanol, *Corynebacterium glutamicum* ISO2 could proliferate even in the presence of 5% isopropanol (FIG. 3). This indicates that a coryneform bacterium is superior to *Escherichia coli* as a host in production of a high concentration of isopropanol.

In the proliferation curve of *Escherichia coli* JM109/pCRC202 (FIG. 3 (*a*)), black circles mean 0% isopropanol, rectangles mean 1% isopropanol, diamonds mean 2% isopropanol, and cross marks mean 3.5% isopropanol (each in LB culture medium, containing 50 μg/mL of chloramphenicol). In the proliferation curve of *Corynebacterium glutamicum* ISO2 (FIG. 3 (*b*)), black circles mean 0% isopropanol, rectangles mean 1% isopropanol, diamonds mean 2% isopropanol, and triangles mean 5% isopropanol (each in A liquid culture medium, containing 5 μg/mL of chloramphenicol and 50 μg/mL of kanamycin).

INDUSTRIAL APPLICABILITY

The transformant of the present invention is useful because it is capable of extremely efficient production of isopropanol from saccharides.

The present invention enables efficient isopropanol production from renewable resources and construction of a new process for industrially producing isopropanol without depending on petroleum resources.

The invention claimed is:

1. A transformant capable of producing isopropanol, which is constructed by transferring the following genes (a) to (d) into *Corynebacterium glutamicum*:
   (a) an exogenous gene which is a DNA comprising the base sequence of SEQ ID NO: 13 and encodes an enzyme having acetyl-CoA acetyltransferase activity;
   (b) an exogenous gene which is a DNA comprising the base sequence of SEQ ID NO: 14 and encodes an enzyme having acetoacetyl CoA:acetate CoA-transferase activity;
   (c) an exogenous gene which is a DNA comprising the base sequence of SEQ ID NO: 15 and encodes an enzyme having acetoacetate decarboxylase activity; and
   (d) an exogenous gene which is a DNA comprising the base sequence of SEQ ID NO: 16 and encodes an enzyme having isopropanol dehydrogenase activity.

2. A transformant, which is *Corynebacterium glutamicum* ISO1 (Accession Number: NITE BP-561), or *Corynebacterium glutamicum* ISO2 (Accession Number: NITE BP-562).

3. A method for producing isopropanol, which comprises a step of culturing the transformant according to claim 1 in a culture medium containing saccharides, and a step of collecting isopropanol from a resulting culture.

4. The transformant according to claim 1, wherein *Corynebacterium glutamicum* is *Corynebacterium glutamicum* R.

* * * * *